US011300564B2

(12) United States Patent
Holmes et al.

(10) Patent No.: US 11,300,564 B2
(45) Date of Patent: *Apr. 12, 2022

(54) IMAGE ANALYSIS AND MEASUREMENT OF BIOLOGICAL SAMPLES

(71) Applicant: Labrador Diagnostics LLC, Healdsburg, CA (US)

(72) Inventors: Elizabeth A. Holmes, Palo Alto, CA (US); Chinmay Pangarkar, Palo Alto, CA (US); Timothy Smith, Palo Alto, CA (US); Karan Mohan, Palo Alto, CA (US); Daniel Young, Palo Alto, CA (US); James Wasson, Palo Alto, CA (US); Samartha Anekal, Palo Alto, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 286 days.

This patent is subject to a terminal disclaimer.

(21) Appl. No.: 15/278,333

(22) Filed: Sep. 28, 2016

(65) Prior Publication Data

US 2017/0115289 A1    Apr. 27, 2017

Related U.S. Application Data

(62) Division of application No. 13/951,063, filed on Jul. 25, 2013, now Pat. No. 9,494,521.

(60) Provisional application No. 61/675,811, filed on Jul. 25, 2012, provisional application No. 61/676,178, filed on Jul. 26, 2012, provisional application No. 61/766,116, filed on Feb. 18, 2013, provisional application No. 61/802,194, filed on Mar. 15, 2013.

(51) Int. Cl.
| | |
|---|---|
| G01N 33/569 | (2006.01) |
| B01L 3/00 | (2006.01) |
| G01N 15/10 | (2006.01) |
| G02B 21/00 | (2006.01) |
| G02B 21/12 | (2006.01) |
| G01N 21/05 | (2006.01) |
| G02B 21/08 | (2006.01) |
| G01N 33/50 | (2006.01) |
| G01N 1/30 | (2006.01) |
| G01N 33/53 | (2006.01) |
| G01N 33/58 | (2006.01) |
| G01N 21/64 | (2006.01) |
| G02B 7/09 | (2021.01) |
| G01N 21/03 | (2006.01) |
| G01N 21/17 | (2006.01) |
| G02B 21/24 | (2006.01) |
| G01N 33/487 | (2006.01) |
| G01N 33/49 | (2006.01) |
| G01N 21/27 | (2006.01) |
| G02B 21/16 | (2006.01) |
| G02B 21/36 | (2006.01) |

(52) U.S. Cl.
CPC .. *G01N 33/56972* (2013.01); *B01L 3/502715* (2013.01); *G01N 1/30* (2013.01); *G01N 15/1012* (2013.01); *G01N 21/0303* (2013.01); *G01N 21/05* (2013.01); *G01N 21/17* (2013.01); *G01N 21/27* (2013.01); *G01N 21/645* (2013.01); *G01N 21/6428* (2013.01); *G01N 21/6458* (2013.01); *G01N 21/6486* (2013.01); *G01N 33/487* (2013.01); *G01N 33/49* (2013.01); *G01N 33/5005* (2013.01); *G01N 33/53* (2013.01); *G01N 33/5308* (2013.01); *G01N 33/56966* (2013.01); *G01N 33/582* (2013.01); *G02B 7/09* (2013.01); *G02B 21/0076* (2013.01); *G02B 21/088* (2013.01); *G02B 21/125* (2013.01); *G02B 21/16* (2013.01); *G02B 21/244* (2013.01); *G02B 21/365* (2013.01); *G01N 2015/1018* (2013.01); *G01N 2021/1738* (2013.01); *G01N 2021/6439* (2013.01); *G01N 2201/061* (2013.01); *G01N 2201/12* (2013.01); *G01N 2333/70589* (2013.01); *G01N 2333/70596* (2013.01)

(58) Field of Classification Search
CPC ............ G01N 15/1012; G01N 21/005; G01N 33/5005; G01N 1/30; G01N 33/5308; G01N 33/53; G01N 33/582; G01N 21/645; G01N 21/0303; G01N 21/17; G01N 21/6458; G01N 21/6486; G01N 33/487; G01N 21/6428; G01N 33/49; G01N 33/56966; G01N 21/27; B01L 3/502715; G02B 21/0076; G02B 21/125; G02B 21/088; G02B 7/09; G02B 21/244; G02B 21/365
See application file for complete search history.

(56) References Cited

U.S. PATENT DOCUMENTS

| | | |
|---|---|---|
| 3,849,654 A | 11/1974 | Malvin |
| 3,854,044 A | 12/1974 | Stay et al. |
| 4,066,362 A | 1/1978 | Carter |

(Continued)

FOREIGN PATENT DOCUMENTS

| | | |
|---|---|---|
| CN | 201156031 | 11/2008 |
| EP | 0781987 A2 | 7/1997 |

(Continued)

OTHER PUBLICATIONS

Office Action dated Mar. 2, 2017 for U.S. Appl. No. 14/508,137.

(Continued)

*Primary Examiner* — Ann Montgomery

(57) ABSTRACT

Methods, devices, systems, and apparatuses are provided for the image analysis of measurement of biological samples.

16 Claims, 17 Drawing Sheets

(56) References Cited

U.S. PATENT DOCUMENTS

| | | |
|---|---|---|
| 4,868,126 A | 9/1989 | Schwartz |
| 4,896,966 A | 1/1990 | Boisseau et al. |
| 5,109,429 A | 4/1992 | Bacus et al. |
| 5,289,255 A | 2/1994 | Mullin et al. |
| 5,292,484 A | 3/1994 | Kelln et al. |
| 5,407,638 A | 4/1995 | Wang |
| 5,414,508 A | 5/1995 | Takahashi et al. |
| 5,534,416 A | 7/1996 | Millard et al. |
| 5,717,778 A | 2/1998 | Chu et al. |
| 5,750,998 A | 5/1998 | Goldman |
| 5,869,689 A | 2/1999 | Zhang et al. |
| 5,932,428 A | 8/1999 | Dubrow et al. |
| 6,079,840 A | 6/2000 | Ono et al. |
| 6,088,097 A | 7/2000 | Uhl |
| 6,396,580 B1 | 5/2002 | Tewes |
| 6,599,475 B1 | 7/2003 | Berndt et al. |
| 6,661,510 B1 | 12/2003 | Hanning et al. |
| 6,690,024 B1 | 2/2004 | Funaoka et al. |
| 7,117,098 B1 | 10/2006 | Dunlay et al. |
| 8,313,713 B2 | 11/2012 | Jacobs et al. |
| 9,122,907 B2 | 9/2015 | Lee et al. |
| 10,823,731 B2 * | 11/2020 | Pangarkar ........ G01N 33/56972 |
| 2001/0028497 A1 | 10/2001 | Uhl |
| 2002/0019062 A1 | 2/2002 | Lea et al. |
| 2002/0192763 A1 * | 12/2002 | Xu .................... C07K 14/47 435/69.7 |
| 2003/0104494 A1 * | 6/2003 | Ravkin ................ C12M 23/12 506/39 |
| 2003/0161572 A1 | 8/2003 | Johnck et al. |
| 2003/0202905 A1 | 10/2003 | Devlin et al. |
| 2003/0205681 A1 | 11/2003 | Modlin |
| 2003/0236458 A1 | 12/2003 | Hochman |
| 2004/0126005 A1 | 7/2004 | Duvdevani et al. |
| 2005/0019842 A1 | 1/2005 | Prober et al. |
| 2005/0030541 A1 | 2/2005 | Erlbacher et al. |
| 2005/0120804 A1 | 6/2005 | Shimi et al. |
| 2005/0153435 A1 | 7/2005 | Archibald |
| 2005/0237605 A1 | 10/2005 | Vodyanoy et al. |
| 2006/0006067 A1 | 1/2006 | Unger |
| 2006/0043301 A1 | 3/2006 | Mantele et al. |
| 2006/0119852 A1 | 6/2006 | Shimizu |
| 2006/0166305 A1 | 7/2006 | Jiang et al. |
| 2006/0184040 A1 | 8/2006 | Keller et al. |
| 2006/0215400 A1 | 9/2006 | Lewis et al. |
| 2007/0035818 A1 * | 2/2007 | Bahatt ................ G01N 21/253 359/366 |
| 2007/0141635 A1 * | 6/2007 | James ................ G01N 33/6872 435/7.2 |
| 2007/0146717 A1 | 6/2007 | Prins et al. |
| 2007/0146870 A1 | 6/2007 | Metzger |
| 2007/0231210 A1 | 10/2007 | Kunuki |
| 2008/0186494 A1 | 8/2008 | Kiesel et al. |
| 2008/0193930 A1 | 8/2008 | Ornatsky et al. |
| 2009/0051901 A1 | 2/2009 | Shen et al. |
| 2009/0170149 A1 | 7/2009 | Viator et al. |
| 2009/0190822 A1 * | 7/2009 | Ortyn ................... G01J 3/2889 382/134 |
| 2010/0014158 A1 | 1/2010 | Nihoshi |
| 2010/0128256 A1 | 5/2010 | Thomson |
| 2010/0315629 A1 | 12/2010 | Knopp et al. |
| 2011/0064628 A1 | 3/2011 | Thomas et al. |
| 2011/0242535 A1 | 10/2011 | Frose |
| 2011/0259744 A1 * | 10/2011 | Moyle .............. G01N 27/44726 204/461 |
| 2012/0002034 A1 | 1/2012 | Matsunobu et al. |
| 2012/0326055 A1 | 12/2012 | Wilson et al. |
| 2013/0088221 A1 | 4/2013 | Van et al. |
| 2014/0030737 A1 | 1/2014 | Holmes et al. |
| 2014/0038206 A1 | 2/2014 | Holmes et al. |
| 2014/0193892 A1 | 7/2014 | Mohan et al. |
| 2014/0273188 A1 | 9/2014 | Mohan et al. |
| 2015/0031051 A1 | 1/2015 | Mohan et al. |
| 2015/0054979 A1 | 2/2015 | Ou et al. |
| 2015/0071541 A1 | 3/2015 | Qutub et al. |
| 2017/0023478 A1 | 1/2017 | Holmes et al. |
| 2017/0146447 A1 | 5/2017 | Mohan et al. |
| 2017/0318216 A1 | 11/2017 | Gladnick et al. |
| 2017/0363851 A1 | 12/2017 | Xu et al. |
| 2018/0259764 A1 | 9/2018 | Watanabe |
| 2019/0339271 A1 | 11/2019 | Mohan et al. |
| 2020/0103406 A1 | 4/2020 | Holmes |
| 2021/0123862 A1 * | 4/2021 | Mohan ............... G01N 15/1468 |
| 2021/0148908 A1 | 5/2021 | Pangarkar |

FOREIGN PATENT DOCUMENTS

| | | |
|---|---|---|
| JP | 2006162427 A | 6/2006 |
| JP | 2007127449 A | 5/2007 |
| JP | 2010091679 A | 4/2010 |
| JP | 2010091809 A | 4/2010 |
| JP | 2011118264 A | 6/2011 |
| TW | 201224425 A | 6/2012 |
| WO | 9743619 A1 | 11/1997 |
| WO | 2002093141 A1 | 11/2002 |
| WO | 2009142312 A1 | 11/2009 |
| WO | 2012119243 A2 | 9/2012 |
| WO | 2012178069 A | 12/2012 |
| WO | 2014018805 A2 | 1/2014 |
| WO | 2014127372 A2 | 8/2014 |

OTHER PUBLICATIONS

Office Action dated Mar. 30, 2017 for U.S. Appl. No. 15/340,637.
Office Action dated May 15, 2017 for U.S. Appl. No. 14/600,630.
510(k) Substantial Equivalence Determination Decision Summary dated Jul. 16, 2015 for "Theranos Herpes Simplex Virus-1 (HSV-1) IgG Assay".
510(k) Substantial Equivalence Determination issued for "Theranos Herpes Simplex Virus-1 IgG Assay" by the FDA on Jul. 7, 2015.
Advisory Action dated Feb. 8, 2016 for U.S. Appl. No. 13/951,449.
Advisory Action dated Apr. 28, 2016 for U.S. Appl. No. 13/951,063.
Advisory Action dated Jul. 26, 2016 for U.S. Appl. No. 14/508,137.
Dhawan et al. Multispectral Optical Imaging of Skin-Lesions for Detection of Malignant Melanomas. Proceeding of the 31st Annual International Conference of the IEEE Engineering in Medicine and Biology Society: Engineering the Future of Biomedicine, EMBC 2009, IEEE, Sep. 3, 2009, pp. 5352-5355.
Diamandis. Theranos phenomenon: promises and fallacies. Clin Chem Lab Med. Jun. 2015;53(7):989-93.
Fuller K. Centers for Medicare and Medicaid Services (CMS). Condition Level Deficiencies Notice—Immediate Jeopardy. Notice to Theranos, Inc. director Dr. Sunil Dhawan. Jan. 25, 2016. https://cdn2.vox-cdn.com/uploads/chorus_asset/file/5969923/Theranos_Inc_Cover_Letter_01-25-2016.0.pdf.
Handoo et al. Tissue flow cytometry in haematological diagnosis. Chapter 41:1-10 International Journal of Laboratory Hematology (Jun. 2012).
International Search Report and Written Opinion dated Sep. 11, 2014 for Application No. PCT/US2014/016962.
Lee et al. Integrated optical molecular imaging system for four-dimensional real-time detection in living single cells, Biosensors and Bioelectronics, Elsevier BV, NL, vol. 31 No. 1, Oct. 27, 2011, pp. 393-398.
Loria K. More skeptical than ever: Experts respond to the government's warning letter to Theranos. Jan. 28, 2016. Tech Insider. http://www.techinsider/io/how-bad-the-cms-letter-to-theranos-really-is-2016-1.
Notice of Allowance dated Mar. 25, 2016 for U.S. Appl. No. 13/951,449.
Notice of Allowance dated Apr. 14, 2016 for U.S. Appl. No. 14/161,639.
Notice of Allowance dated Jun. 23, 2016 for U.S. Appl. No. 13/951,063.
Notice of Allowance dated Aug. 10, 2016 for U.S. Appl. No. 14/161,639.
Office Action dated Jan. 15, 2016 for U.S. Appl. No. 14/508,137.
Office Action dated Jan. 4, 2016 for U.S. Appl. No. 14/161,639.
Office Action dated Nov. 5, 2015 for U.S. Appl. No. 13/951,449.

(56) References Cited

OTHER PUBLICATIONS

Office Action dated Feb. 24, 2016 for U.S. Appl. No. 13/951,063.
Office Action dated May 12, 2016 for U.S. Appl. No. 14/508,137.
Office Action dated May 6, 2015 for U.S. Appl. No. 13/951,449.
Office Action dated Jun. 12, 2015 for U.S. Appl. No. 14/161,639.
Office Action dated Jun. 5, 2015 for U.S. Appl. No. 14/508,137.
Office Action dated Jul. 8, 2015 for U.S. Appl. No. 13/951,063.
Office Action dated Sep. 21, 2015 for U.S. Appl. No. 14/508,137.
Office Action dated Sep. 22, 2016 for U.S. Appl. No. 14/167,964.
Office Action dated Sep. 9, 2016 for U.S. Appl. No. 14/508,137.
Plebani. Evaluating and using innovative technologies: a lesson from Theranos? Clin Chem Lab Med. Jun. 2015;53(7):961-2.
Ramsey L. Theranos has a week to respond to the searing report about its business. Business Insider. Feb. 5, 2016. http://www.businessinsider.com/theranos-response-to-cms-2016-2.
Rappleye E. Theranos gets extension to fix issues following CMS investigation. Becker's Hospital Review. Feb 8, 2016. http://www.beckershospitalreview.com/hospital-management-adminstration/theranos-gets-extension-to-fix-issues-following-cms-investigation.html.
The International Search Report and the Written Opinion dated Mar. 24, 2014 for Application No. PCT/US2013/052141.
Thompson, Fluorescence Correlation Spectroscopy, Topics in Fluorescence Spectroscopy, Jan. 1, 2002, Kluwer Academic Publishers, Boston.
U.S. Appl. No. 14/600,630, filed Jan. 20, 2015.
Office Action dated Oct. 6, 2017 for U.S. Appl. No. 14/630,544.
Office Action dated Feb. 9, 2018 for U.S. Appl. No. 15/340,637.
Office Action dated Jun. 20, 2017 for U.S. Appl. No. 14/167,964.
Office Action dated Jun. 28, 2018 for U.S. Appl. No. 15/184,923.
Office Action dated Jun. 5, 2018 for U.S. Appl. No. 14/508,137.
Office Action dated Aug. 15, 2018 for U.S. Appl. No. 14/600,630.
Office Action dated Aug. 15, 2018 for U.S. Appl. No. 15/340,637.
Office Action dated Mar. 14, 2019 for U.S. Appl. No. 14/600,630.
Office Action dated May 30, 2019 for U.S. Appl. No. 15/340,637.
Office Action dated Jul. 8, 2019 for U.S. Appl. No. 15/664,580.
Office Action dated Dec. 20, 2019 for U.S. Appl. No. 14/600,630.
Office Action dated Oct. 16, 2020 for U.S. Appl. No. 16/447,540.
Office Action dated Oct. 27, 2020 for U.S. Appl. No. 16/382,489.
Office Action dated Apr. 9, 2021 for U.S. Appl. No. 16/382,489.
Office Action dated May 17, 2021 for U.S. Appl. No. 16/447,540.
Office Action dated Jul. 26, 2021 for U.S. Appl. No. 17/011,197.

* cited by examiner

IMAGE ANALYSIS AND MEASUREMENT OF BIOLOGICAL SAMPLES

This application claims priority to, and the benefit under 35 U.S.C. § 119(e) of, U.S. Patent Application Ser. No. 61/675,811, filed Jul. 25, 2012; U.S. Pat. App. Ser. No. 61/676,178, filed Jul. 26, 2012; U.S. Patent Application 61/766,116, filed Feb. 18, 2013; and U.S. Patent Application 61/802,194, filed Mar. 15, 2013; the disclosures of all of which patent applications are hereby fully incorporated by reference in their entireties for all purposes.

BACKGROUND

Analysis of biological samples from a subject may be important for health-related diagnosing, monitoring and/or treating of the subject. A variety of methods are known for the analysis of biological samples. However, in order to provide better diagnosing, monitoring, and/or treating of subjects, improvements in the analysis of biological samples are desired.

INCORPORATION BY REFERENCE

All publications, patents, and patent applications mentioned in this specification are herein incorporated by reference to the same extent as if each individual publication, patent, or patent application was specifically and individually indicated to be incorporated by reference.

COPYRIGHT

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2013 Theranos, Inc.

SUMMARY

Methods, devices, systems, and apparatuses are described herein for image analysis and/or measurement of biological samples.

In one embodiment, a method for the measurement of a component of interest in cells of a cellular population in a sample is provided, including: a) obtaining a quantitative measurement of a marker present in cells of the cellular population in the sample; b) based on the measurement of part a), determining, with the aid of a computer, an approximate amount of cells in the cellular population present in the sample; c) based on the results of part b), selecting an amount of reagent to add to the sample, wherein the reagent binds specifically to the component of interest in cells of the cellular population and is configured to be readily detectable; d) based on the results of part c), adding the selected amount of the reagent to the sample; e) assaying cells in the sample for reagent bound to the compound of interest; and f) based on the amount of reagent bound to the compound of interest, determining the amount of the component of interest in cells of the cellular population of the sample. In an embodiment of the method, the reagent of part c) is an antibody.

In another embodiment, a method for focusing a microscope is provided, including: a) mixing a sample containing an object for microscopic analysis with a reference particle having a known size, to generate a mixture containing the sample and reference particle; b) positioning the mixture of step a) into a light path of a microscope; c) exposing the mixture of step a) to a light beam configured to visualize the reference particle; and d) focusing the microscope based on the position of the reference particle within the mixture.

In yet another embodiment, provided herein is a method for identifying a cell in a sample containing a plurality of cells, including: a) assaying a cell of the plurality of cells for at least one of: (i) the presence of a cell surface antigen; (ii) the amount of a cell surface antigen; or (iii) cell size; b) assay the cell of a) for at least one of: (i) nuclear size; or (ii) nuclear shape; and c) assaying the cell of a) and b) for quantitative cell light scatter, wherein the combination of information from steps a), b) and c) is used to identify the cell in the sample containing a plurality of cells.

In yet another embodiment, provided herein is a system of a detector assembly for use with a sample holder that holds a sample to be examined. In one non-limiting example, the sample holder is a cuvette that has features and/or materials in it that enable the cuvette to be engaged and moved from one location to the detector assembly. In some embodiments, the detector assembly has a first surface that is configured to engage a surface of the sample holder in a manner such that the interface between the two does not create optical interference in the optical pathway from the detector assembly to the sample in the sample holder. In one embodiment, there may be more than one location on the detector assembly for one or more of the sample holders. Some embodiments may have the same sample holder for each of the locations. Optionally, some embodiments may have different sample holders for at least some of the locations associated with the detector assembly.

In one embodiment described herein, a sample holder is provided herein such as but not limited to a cuvette with optical properties, dimensions, materials, and/or physical features that allow for it to hold the sample for analysis by the detector assembly while keeping it physically separate from and not in direct contact with the detector assembly. This can be particularly useful for sample fluids that contain shaped members therein.

In one embodiment described herein, the detector assembly may be a multi-channel microscopy unit that is configured to obtain shape of cell, physical, optical, and biochemical properties all in the same device. It can provide both quantitative info, and descriptive info. One embodiment of the detector assembly may use multiple markers of the same color, and then deconvolute signals—this allows reduction in number of spectral channels and light sources.

It should be understood that some embodiments herein may have a sample holder such as but not limited to a cuvette with physical features in the shape of the cuvette material that increase darkfield illumination where some features are for light reflectance, optionally some for mechanical support. The system herein can use both epi (direct) and trans (reflected) illumination in darkfield imaging. This differs from traditional darkfield imaging which uses mainly epi, not trans illumination. Thus, the combo of epi and trans illumination, wherein the trans illumination originates from the same light source as the epi illumination differs from known systems. Optionally, the use of a shaped sample holder such as the cuvette can be used to provide the trans illumination. Optionally, the trans illumination is at a non-negligable level [at least x amount]. Optionally, one embodiment may add an actual reflective surface to increase trans light generated. The dark field light source may be an LED, laser, or other illumination source that can provide the desired excitation wavelength(s).

In one embodiment, the combination of the microscope objective and ringlight (for darkfield microscopy) is at a physical distance between them that enables a compact size for the detector assembly.

In yet another embodiment, information from the cytometry assay, either from the sample preparation phase and/or from the analysis phase, is used to guide/trigger a secondary procedure. One procedure may be to provide an alert for direct human review. Another is to use an estimated cell count or other information from the sample preparation stage to be information used to guide assay performance in another procedure.

Techniques for counting cells can also provide ways to deal with uneven cuvettes. One method comprises using: a) volume-metered channel to introduce a known volume into a channel. The method may include counting all cells in the cuvette. Since one knows the volume of sample, one also knows the concentration of cells in volume (this may be performed in hydrophobic containers or cuvettes with chambers with such surfaces). Another method comprises: b) ratio-based metric to mix sample with a known amount of beads, which is used to calculate the concentration of cells in the sample based on the number of beads observed.

In yet another embodiment described herein, a method is provided comprising measuring formed blood components such as but not limited to RBC volume by swelling the formed blood components such as but not limited to RBCs into spheres, and measuring volume by darkfield microscopy.

In yet another embodiment described herein, a method is provided comprising measuring platelet volume. The method may including labeling platelets with fluorescent dye and measuring the size of signal. One then add beads to sample of known size and compare to platelet.

It should be understood that embodiments in this disclosure may be adapted to have one or more of the features described in this disclosure.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1A:
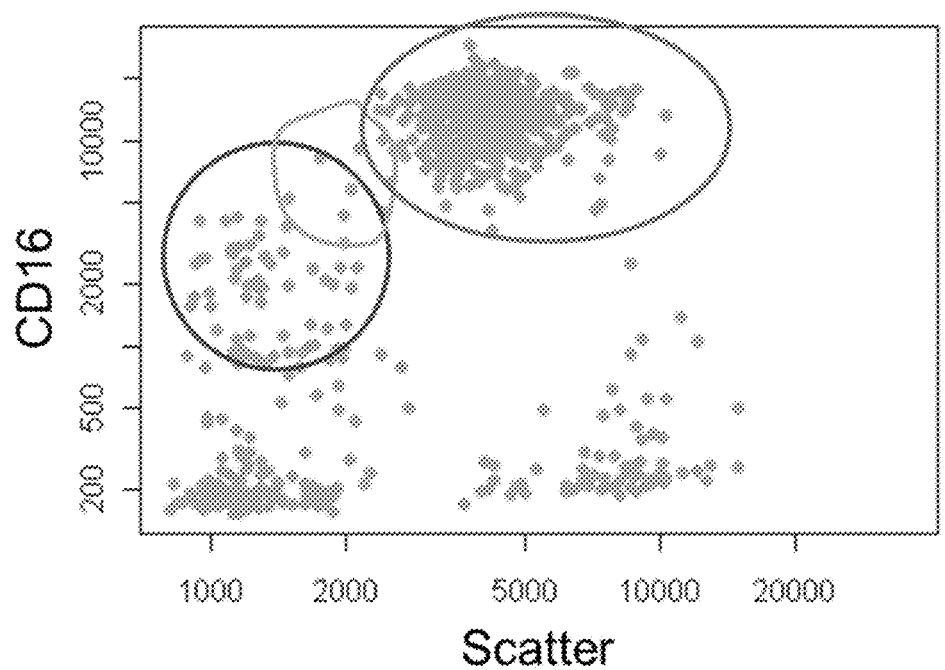
FIG. 1A shows a plot of side scatter intensity (x-axis) vs. fluorescence intensity of a mixture cells including natural killer cells and neutrophils labeled with a fluorescent binder that recognizes CD16.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "sample" may be but is not limited to a blood sample, or a portion of a blood sample, may be of any suitable size or volume, and is preferably of small size or volume. In some embodiments of the assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

The term "cells," as used in the context of biological samples, encompasses samples that are generally of similar sizes to individual cells, including but not limited to vesicles (such as liposomes), cells, virions, and substances bound to small particles such as beads, nanoparticles, or microspheres.

Quantitative Microscopy

In some embodiments, methods, systems, and devices are provided herein for quantitative microscopy. Quantitative microscopy may involve one or more of quantitative fluorescence microscopy, quantitative dark field microscopy, quantitative bright field microscopy, and quantitative phase contrast microscopy methods to measure one or more cellular attributes. Any of these methods may provide morphometric information regarding cells. Such information may be measured quantitatively. In some embodiments, for quantitative microscopy, a sample is analyzed by two or more of quantitative fluorescence microscopy, quantitative dark field microscopy, quantitative bright field microscopy, and quantitative phase contrast microscopy. Quantitative microscopy may include use of image analysis techniques and/or statistical learning and classification methods to process images obtained by microscopy.

Multiple different cellular attributes may be measured during quantitative microscopy. Cellular attributes that may be measured include, without limitation:

Physical attributes: e.g. cell size, volume, conductivity, low and high angle scatter, and density.

Morphological attributes: e.g. cell shape, area, size, and lobularity; nucleus shape area, size, and lobularity; mitochondria shape, area, size, and lobularity; and ratio of nuclear volume to cell volume.

Intracellular attributes: e.g. nucleus centroid/cell centroid distance (i.e. distance between the center of the nucleus and the center of the cell), nucleus lobe centroid distance (i.e. distance between the center of different lobes of the nucleus), distribution of proteins with the cells (e.g. actin, tubulin, etc.), and distribution of organelles within the cells (e.g. lysosomes, mitochondria, etc.).

Biochemical attributes: e.g. expression level of cellular proteins, cell surface proteins, cytoplasmic proteins, nuclear proteins, cellular nucleic acids, cell surface nucleic acids, cytoplasmic nucleic acids, nuclear nucleic acids, cellular carbohydrates, cell surface carbohydrates, cytoplasmic carbohydrates, and nuclear carbohydrates.

In some embodiments, methods, systems, and devices are provided herein for the quantitative measurement of two, three, four, five or more attributes of cells in a sample, wherein the attributes are selected from physical attributes, morphological attributes, intracellular attributes, and biochemical attributes. In some embodiments, methods, systems, and devices are provided herein for the quantitative measurement of two, three, four, five or more attributes of cells in a sample, wherein the attributes are selected from: cell size, cell volume, cell conductivity, cell low angle light scatter, cell high angle light scatter, cell density, cell shape, cell area, cell lobularity, nucleus shape, nucleus area, nucleus size, nucleus lobularity, mitochondria shape, mitochondria area, mitochondria size, mitochondria lobularity, ratio of nuclear volume to cell volume, nucleus centroid/cell centroid distance, nucleus lobe centroid distance, distribution of proteins with the cells (e.g. actin, tubulin, etc.), distribution of organelles within the cells (e.g. lysosomes, mitochondria, etc.), expression level of a cellular protein, expression level of a cell surface protein, expression level of a cytoplasmic protein, expression level of a nuclear protein, expression level of a cellular nucleic acid, expression level of a cell surface nucleic acid, expression level of a cytoplasmic nucleic acid, expression level of a nuclear nucleic acid, expression level of a cellular carbohydrate, expression level of a cell surface carbohydrate, expression level of a cytoplasmic carbohydrate, and expression level of a nuclear carbohydrate.

In some embodiments, methods are provided for the quantitative measurement of two, three, four, five, or more attributes of cells in a biological sample by microscopy, wherein the method may include one or more of the following steps or elements. The attributes of the cells quantitatively measured may be selected from the attributes listed in the immediately above paragraph. The biological sample may be pre-treated prior to microscopy. Pre-treatment may include any procedure to aid in the analysis of the sample by microscopy, including: treatment of the sample to enrich for cells of interest for microscopy, treatment of the sample to reduce components in the sample which may interfere with microscopy, addition of material to the sample to facilitate analysis of the sample by microscopy (e.g. diluents, blocking molecules to reduce non-specific binding of dyes to cells, etc.). Optionally, prior to microscopy, a sample may be contacted with one or more binders that specifically bind to a cellular component. Binders may be directly linked to a dye or other particle for the visualization of the binder. A sample may also be contacted with a secondary binder, which binds to the binder which binds to the cellular component. A secondary binder may be directly linked to a dye or other particle for the visualization of the binder. Prior to microscopy, a sample may be assayed in a spectrophotometer. For microscopy, a biological sample containing or suspected of containing an object for microscopic analysis may be introduced into a sample holder, such as a slide or a cuvette. The sample holder containing a sample may be introduced into a device configured to perform quantitative microscopy on the sample. The microscope may be coupled with an image sensor to capture images generated through the microscope objective. In the device, multiple images of the sample may be acquired by microscopy. Any one or more of quantitative fluorescence microscopy, quantitative dark field microscopy, quantitative bright field microscopy, and quantitative phase contrast microscopy may be used to obtain images of the sample. Optionally, images of the entire sample in the sample holder may be acquired by microscopy. Multiple fields of view of the microscope may be required capture images of the entire sample in the sample holder. The sample holder may move relative to the microscope or the microscope may move relative to the sample holder in order to generate different field of views in order to examine different portions of the sample in the sample holder. Multiple images of the same field of view of the sample in the sample holder may be acquired. Optionally, multiple filters may be used with the same type of microscopy and the same field of view of the sample, in order to acquire different images of the same sample which contain different information relating to the sample. Filters that may be used include, without limitation band-pass and long pass filters. Filters may permit the passage of certain wavelengths of light, and block the passage of others. Optionally, multiple types of microscopy (e.g. fluorescence, dark field, bright field, etc.) may be used to acquire images of the same field of view of the sample, in order to acquire different images of the same sample which contain different information relating to the sample. Optionally, video may be used to collect microscopy images. Optionally, microscopy images may be collected in 3-D. For microscopy performed as described herein, the device or system may be configured to link information relating to a cell in one image of the sample to the same cell in a different image of the sample. Based on different images of the same sample and/or same cells, multiple attributes of cells in the sample may be determined. In some aspects, the combination of multiple attributes/multiple pieces of information about cells in a sample may be used to reach a clinical decision and/or to draw a conclusion about the cells that would not be possible based on information from only a single attribute of the cells.

In some embodiments, devices and systems are provided for the quantitative measurement of two, three, four, five, or more attributes of cells in a biological sample by microscopy. In some embodiments, the device or system contains both a microscope or cytometer and a spectrophotometer. The device or system may further contain a fluid handling apparatus, which is configured to move sample between a spectrophotometer and a microscope or cytometer. In some embodiments, devices and systems for performing the methods disclosed herein are configured as described in U.S. patent application Ser. No. 13/244,947, which is hereby incorporated by reference in its entirety. Although the foregoing has been described in the context of a cell, it should also be understood that some or all of the foregoing may also be applied to crystals or other cell-sized objects that may be found in a sample.

Dynamic Dilution

In some embodiments, methods, systems, and devices are provided herein for dynamic dilution of cell-containing samples.

By way of non-limiting example, a method for dynamic dilution of a sample may include one or more of the following steps or elements such that a desired number or concentration of cells or objects in the sample is determined and this information is used as a factor in adjusting downstream sample processing. In this non-limiting example, one or more stains may be added to a biological sample containing cells. The mixture of stain and sample may be incubated. The cells in the mixture of stain and sample may be washed to remove excess (unbound) stain. The stained, washed cells may be prepared in a desired volume for further analysis. The stained, washed cells may be analyzed to determine the approximate number or concentration of cells in the sample or a portion thereof. Based on the number or concentration of stained cells in the sample or portion thereof, a volume of sample may be obtained for further analysis, such that a desired number or concentration of cells for further analysis is obtained. In some embodiments, samples may be diluted as described in U.S. patent application Ser. No. 13/355,458, which is hereby incorporated by reference in its entirety.

In one embodiment as described herein, it is desirable to provide another detection technique such as but not limited to fluorescence-based method for enumerating cells, to estimate cell concentration in place of using a cell counter. This estimate is describe because, for accurate and reproducible staining of patient samples, it is often desirable that stains (DNA dyes/antibodies/binders/etc.) are optimally titered for a specific number/concentration of cells. For example, a known concentration of stain will be applied to a specific number of cells (e.g. 0.2 micrograms of stain per one thousand WBCs). After an incubation period, the sample will be washed to remove excess (unbound) dye, prepared at the appropriate cell density, and imaged.

In this non-limiting example, to make an estimate of cell concentration for a targeted cell type, a sample is non-destructively measured with a different modality from that used for cytometry, such as but not limited to a spectrophotometer, in order to inform sample processing for the cytometric assay. The method may comprise selecting another marker unique to the cell population of interest. In one non-limiting example, for B-cells, one may choose CD20. The process comprises labeling the sample with anti-CD20 binders conjugated to a different colored fluorophore than CD5. One then measures the fluorescent signal of this sample non-destructively and rapidly using a device such as but not limited to a fluorescence spectrophotometer. Using calibration, it is possible to predict the concentration of B-cells with limited accuracy to provide the estimate. In one non-limiting example, the calibration may correlate signal strength with the number of cells for that type of signal. The creation of these calibration curves can be used to estimate the number of cells or object. Other techniques for estimating number of cells based on an overall signal strength such as but not limited to optical, electrical, or the like are not excluded. Based on the approximate concentration of B-cells, the system can estimate the appropriate amount and concentration of anti-CD5 binder so that proportional relationship between CD5 expression and CD5 fluorescence is maintained. In this manner, the stain and staining procedure can be optimized/normalized for a particular cell number.

To maximize the use of patient samples (finger stick blood, equal or less than 120 uL), it is desirable to develop methods whereby the number of WBCs contained within a given volume of blood, can be enumerated (i.e. WBCs/uL). This allows the number of WBCs to be determined prior to adding stains. Once determined, an exact number of cells can be aliquoted for incubation with a known concentration of stain(s), yielding optimal resolution of cell subpopulations.

Example 1—this example comprises determining the ploidy of cells (enumerate cells via fluorophore-conjugated antibody staining). In this non-limiting example, it is desired to enumerate the WBCs in a blood sample so that a specific number of WBCs can be stained with a predetermined concentration of DNA dye (i.e. DAPI or propidium iodide). The method comprises counting WBCs using a fluorophore-conjugated antibody and a spectrophotometer (similar to the dynamic dilution performed in the cytometry/CBC assay for WBCs). It should be understood that this approach may be helpful when staining cells with a DNA dye and determining ploidy, where the ratio of cell number to DNA dye concentration (cell #: [DNA dye]) is desirable for generating comparable and consistent data. Given that the number of cells per microliter of blood vary within a healthy population, it is typically desirable to determine the number of WBCs per microliter before attempting to stain for ploidy.

In one embodiment, the procedure comprises using cells, where they will first be stained with a fluorophore-conjugated antibody (i.e. a ubiquitously expressed, such as CD45, or a subpopulation specific antibody, such as CD3 for T cells) that is spectrally distinct/distant from the emission of the DNA dye. After an incubation period, the sample will be washed to remove excess (unbound) antibody, prepared in the appropriate volume, and analyzed via a spectrophotometer. The resulting data will allow for the WBCs to be enumerated/determined, so that a specific volume of blood can be aliquoted (yielding a particular/desired number of WBCs) and stained with a DNA dye.

Example 2—this example comprises determining the number of cells (via DNA staining) prior to surface staining. Additional details may also be found in the cell enumeration section herein below. It is sometimes desirable to enumerate the WBCs in a blood sample so that a specific number of WBCs can be stained with optimal concentrations of antibodies. In one embodiment, the method comprises counting WBCs using a DNA dye and a spectrophotometer (similar to the dynamic dilution performed in the cytometry/CBC assay for WBCs).

Alternatively, if the number of cells per microliter was determined prior to staining, then a known number of cells could be aliquoted and stained for each sample, regardless of (i) variation within a healthy population and (ii) disease state. To determine the number of cells per microliter of blood, it may be possible to use DNA dyes such as DRAQ5 or propidium iodide. After washing away the unbound dye, a spectrophotometer can be used to determine the number of nucleated (DRAQ5+) cells per microliter of blood.

In one non-limiting example, the procedure uses cells wherein the cells will first be stained with a DNA dye (ie DRAQ5 or propidium iodide) that is spectrally distinct/distant from the emission of the fluorophore-conjugated antibodies that will be used. After an incubation period, the sample will be washed to remove excess (unbound) DNA dye, prepared in the appropriate volume, and imaged via a spectrophotometer. The resulting data will allow for the WBCs to be enumerated/determined, so that a specific volume of blood can be aliquoted (yielding a particular/desired number of WBCs) and stained with antibodies titrated for the particular/desired number of WBCs.

Dynamic Staining

In some embodiments, methods, systems, and devices are provided herein for dynamic staining of cell-containing samples.

Measurement of a Component of Interest in Cells of a Cellular Population

In one embodiment, a method for dynamically staining a cell sample relates to a method for the measurement of a component of interest in cells of a cellular population in a sample.

As used herein, a "component of interest" refers to any type of molecule that may be present in a cell. "Components of interest" include proteins, carbohydrates, and nucleic acids. Typically, a "component of interest" is a specific species of molecule, such as a particular antigen. Non-limiting examples of "components of interest" of a cell include: CD5 protein, CD3 protein, etc.

As used herein, a "cellular population" refers to any grouping of cells, based on one or more common characteristics. A "cellular population" may have any degree of breadth, and may include a large number of cells or only a small number of cells. Non-limiting examples of "cellular populations" include: red blood cells (RBCs), white blood cells, B-cells, CD34+ B-cells, etc.

In some circumstances, it may be desirable to quantitatively measure a component of interest in cells of a certain cellular population in a sample from a subject. For example, it may be desirable to measure the extent of CD5 (the "component of interest") expression in B-cells (the "cellular population") in a sample of cells from a subject having chronic lymphocytic leukemia. Detection and/or measurement of the level of a component of interest may involve use of a binder molecule that has affinity for the specific component of interest, such an antibody or single chain variable fragment ("scFv"). In order to accurately measure the level of a specific component of interest in cells in a method involving the use of a binder molecule, it may be advantageous to expose the cells to the binder molecule at a specific ratio or range of ratios of binder molecule to target component of interest. For example, it may be desirable to provide an amount of binder to a collection of cells such that there is a linear relationship between the amount of component of interest in the cells and the amount of binder which binds to the component of interest in the cells. For example, it may be undesirable to have too little binder (such that there is not enough binder to bind to all of the components of interest in the cells) or to have too much binder (such that the binder binds non-specifically to the cells).

Using traditional methods, it may be difficult to provide an appropriate level of binder to a sample in order to accurately measure the amount of component of interest in a cellular population in the sample, due to the fact that the size of the cellular population and/or component of interest in the sample may vary significantly between different samples. In contrast, provided herein are methods, devices, and systems for dynamically staining cell samples to accommodate samples containing a wide range of cellular populations and components of interest.

In one embodiment, a method for the measurement of a component of interest in cells of a cellular population in a sample is provided. The method is not limited to but may include one or more of the following steps.

First, a quantitative or semi-quantitative measurement of a marker present in cells of the cellular population may be obtained. The marker may be any marker which is present in the cellular population of interest, and it may be a marker exclusively present in the cellular population of interest (i.e. not present in any other cell types in the sample). Measurement of the marker may be by any method, provided the method does not destroy the sample, and may use any system or device. A binder which recognizes the marker may be mixed with the sample. The binder may have a molecule attached to facilitate detection of the binder (e.g. a fluorescent marker). In an example, the marker may be detected and/or measured by fluorescence spectrophotometry. In embodiments in which the binder has a fluorescent label and the marker is measured by fluorescence spectrophotometry, fluorescence spectrophotometry may be used to measure a bulk fluorescence from the sample or a portion thereof, rather than to measure fluorescence from individual cells.

Second, based on the quantitative or semi-quantitative measurement of the marker present in cells of the cellular population, an approximate amount or concentration of cells of the cellular population present in the sample may be determined. The approximate number or concentration of cells in the cellular population present in the sample may be determined, for example, through the use of a calibration curve. Calibration curves may be prepared and/or may be available for different markers/binder combinations. Calibration curves may be developed, for example, by measuring the signal from known numbers of cells having a certain marker and bound with a certain binder. In some embodiments, the approximate amount or concentration of cells of the cellular population present in the sample may be determined with the aid of a computer. In some aspects, the approximate number or concentration of cells in the cellular population present in the sample may be determined at no more than about 10, 20, 30, 40, 50, 60, 70, 80, 90, 100, 150, 200, 250, 300, 400, or 500% off the true concentration.

Third, based on the determined amount or concentration of cells in the cellular population present in the sample, an amount of a reagent to add to the sample may be selected, wherein the reagent binds specifically to the component of interest in cells of the cellular population. The reagent may be any molecule that binds specifically to the component of interest. For example, the reagent may be a binder, such as an antibody. The reagent may be configured such that it may be readily detected (e.g. by fluorescence or luminescence) and/or such that under at least some circumstances, it produces a detectable signal. In some embodiments, the reagent may be attached to a molecule to facilitate detection of the reagent. The amount of reagent added to the sample may be any amount. In some embodiments, an amount of reagent may be added to the sample such that there is an approximately linear relationship between the level of the component of interest in individual cells of the cellular population and the signal produced by the reagents bound to the components of interest in individual cells of the cellular population.

Fourth, after the amount of a reagent to add to the sample is selected, the selected amount of reagent may be added to the sample.

Fifth, cells in the sample may be assayed for reagent bound to the compound of interest.

Sixth, based on the amount of reagent bound to the component of interest, the amount of the component of interest in cells of the cellular population of the sample may be determined.

In some embodiments, the fifth and sixth steps may be performed together such that the measurement of the amount of reagent bound to the component of interest is sufficient to identify the amount of the component of interest in cells of the cellular population of the sample.

In other embodiments, provided herein are systems and devices for the dynamic staining of samples. The systems and devices may contain, without limitation, a spectrophotometer and a fluorescence microscope. In an embodiment, a system or method for dynamic staining of samples may be configured as described in U.S. patent application Ser. Nos. 13/244,947 or 13/355,458, which are hereby incorporated by reference in their entirety. In an embodiment, the systems and devices may be automated to determine an amount of a reagent to add to a sample to determine the amount of a component of interest in cells of a cellular population in a sample, based on a measurement of an amount of a marker present in cells of the cellular population. In another embodiment, the systems and devices may be automated to determine an amount of a reagent to add to a sample to determine the amount of a first component in cells of a cellular population in a sample, based on a measurement of an amount of a second component in the cells of the cellular population in a sample.

Context-Based Autofocus

In some embodiments, methods, systems, and devices are provided herein for context-based microscopy autofocus.

The length of many clinically relevant objects in biological samples spans a wide range. For example, bacteria are commonly about 1 µm in length, erythrocytes are commonly about 6-8 µm in length, leukocytes are commonly about µm 10-12 in length, epithelial cells may be about 100 µm in length, and cast and crystals may be about 200-300 µm in length. In addition, there are many amorphous elements such as urinary mucus which exist as strands or filaments which may range from about 10-400 µm in length.

A challenge in microscopy is to acquire precise images of fields of view that contain an unknown and arbitrary composition of objects of various sizes, such as those described above. Since the depth of focus of many microscopy objectives is limited (typically about 1-10 µm), for a given field of view containing elements of various sizes, multiple focal planes for the given field of view may need to be acquired in order to obtain accurate sharp images of the various elements within the field of view. A problem with many traditional autofocus methods is that they are designed to focus on the dominant feature in a field of view, so that the sharpness of that feature can be maximized. Such methods may be ineffective for capturing elements of various sizes in a sample.

In one embodiment, a method is provided for context-based microscopy autofocus, which includes mixing a reference particle of a known size with a sample for microscopy. The reference particle may be detected during microscopy, and used to achieve focusing. By use of the reference particles to achieve focusing, focal planes may be selected independent from the overall image composition. In one aspect, the method may be useful to achieve focusing on a sample having an unknown composition of elements. In another aspect, the method may support the generation of precise planes of focus, independent of the precision of the microscope or microscopy-related hardware. For example, when a plane of focus is selected based on feedback from the sharpness of the reference particles within a field of view, precise focusing on various elements within a sample may be achieved, regardless of the level of accuracy or precision of the focusing hardware [e.g. the microscope objective actuation, the shape of a sample holder (e.g. a cuvette or slide), or the non-uniformity of a sample holder].

In an embodiment, a reference particle may contain or be labeled with a molecule to facilitate detection of the particle during microscopy. In one example, a reference particle may be labeled with or contain a fluorescent molecule. The fluorescent molecule may absorb light at a first wavelength of light, and, in response to the absorbance of the first wavelength of light, it may emit light at a second wavelength. In an embodiment, a sample mixed with a reference particle may be exposed to a wavelength of light capable of exciting a fluorescent molecule in a reference particle of interest and emitted light from the fluorescent molecule may be measured. Specific fluorescence from a reference particle may be used to detect reference particles, and information from detected reference particles in a sample may be used for autofocusing.

Reference particles may be of any shape, such as spherical or cuboid. Reference particles include, without limitation, beads and microspheres. Reference particles may be of any size, such as with a diameter or length of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 20, 30, 40, 50, 60, 70, 80, 90, 100, 125, 150, 175, 200, 250, 300, 350, 400, 450, or 500 µm. Reference particles may contain any material, such as polystyrene, polystyrene, latex, acrylic, or glass.

In one embodiment, a method for focusing a microscope is provided, which may include one or more of the following steps. First, a sample containing an object for microscopic analysis (e.g. bacteria, erythrocytes, etc.) may be mixed with a reference particle. The reference particle may contain or be labeled with a molecule to facilitate the detection of the particle, such as a fluorophore. Second, the mixture containing the reference particle and the sample may be positioned into a light path of a microscope, for example in cuvette or slide. Optionally, the reference particle may sink to the bottom of the sample in the cuvette or slide, such that the reference particle rests on the lowest surface of the cuvette or slide which is in contact with the sample. The microscope may be of any type, including a fluorescent microscope. Third, the mixture may be exposed to a light beam configured to visualize the reference particle. The light beam may be of any type, and may be of any orientation relative to the reference particle. For example, the light beam may be at a wavelength capable of exciting a fluorophore within or attached to the reference particle. Exposure of the reference particle to the light beam may result in, for example, the generation and emission of light at a particular wavelength from the reference particle and/or scattering of light from the reference particle. Fourth, light emitted or scattered from the reference particle may be detected by the microscope, and this information may be used in order to determine the position of the reference particle within the mixture and/or to focus the microscope. Optionally, the microscope may be focused into a plane of focus suited for objects of similar size to the reference particle. An image from the microscope may be obtained by an image sensor. The image may be saved and/or or used for image analysis.

In some embodiments, a plurality of reference particles may be added to a sample. The reference particles may be all of the same size, or they may be of different sizes. In some embodiments, reference particles of different sizes contain different fluorophores. Different fluorophores may have different absorption wavelengths, different emission wavelengths, or both.

In an embodiment, a method for focusing a microscope is provided, including mixing more than one reference particle of known size with a sample for microscopy, wherein at least two of the reference particles are of different sizes and contain different fluorophores. The method may include one or more of the following steps. First, a sample containing an object for microscopic analysis may be mixed with two or more reference particles, wherein at least two of the reference particles are of different sizes and contain different fluorophores (i.e. the "first reference particle" and the "second reference particle"). Second, the mixture containing the reference particles and the sample may be positioned into the light path of a microscope. The microscope may be of any type, including a fluorescent microscope. Third, the mixture may be exposed to a light beam configured to visualize the first reference particle. The light beam may be of any type, and may be of any orientation relative to the first reference particle. For example, the light beam may be at a wavelength capable of exciting a fluorophore within or attached to the first reference particle. Exposure of the first reference particle to the light beam may result in the generation and emission or scattering of light at a particular wavelength from the first reference particle. Fourth, light emitted or scattered from the first reference particle may be detected, and this information may be used in order to determine the position of the first reference particle within the mixture and/or to focus the microscope into a first plane of focus suited for objects of similar size to the first reference particle. Optionally, an image of the first focal plane may be obtained by an image sensor. The image may be saved and/or or used for image analysis. Fifth, the mixture may be exposed to a light beam configured to visualize the second reference particle. The light beam may be of any type, and may be of any orientation relative to the second reference particle. Exposure of the second reference particle to the light beam may result in the generation and emission or scattering of light at a particular wavelength from the second reference particle. Sixth, light emitted or scattered from the second reference particle may be detected, and this information may be used in order to determine the position of the second reference particle within the mixture and/or to focus the microscope into a second plane of focus suited for objects of similar size to the second reference particle. Optionally, an image of the second focal plane may be obtained by an image sensor. The image may be saved and/or or used for image analysis.

In other embodiments, provided herein are systems and devices for context-based microscopy autofocus. The systems and devices may contain, without limitation, a fluorescence microscope. In an embodiment, the systems and devices may be automated to add a reference particle having a known size to a sample for microscopic analysis to form a mixture, to position the mixture into the light path of a microscope, to expose the mixture to a light beam configured to visualize the reference particle, to determine the position of the reference particle within the mixture and/or to focus the microscope based on the position of the reference particle within the mixture. In an embodiment, a system or method for context-based microscopy autofocus may be configured as described in U.S. patent application Ser. Nos. 13/244,947 or 13/355,458, which are hereby incorporated by reference in their entirety.

Cell Counting/Enumerating Cells

In some embodiments, methods, systems, and devices are provided herein for enumerating cells in a sample.

Certain traditional methods for staining cell-containing samples involve staining a specific volume of a sample (e.g. blood) with a particular concentration or amount of stain. This may be referred to as "volumetric staining." Volumetric staining has a number of shortcomings, including: (i) it fails to address normal variations in cell subpopulations between different subjects (e.g. different healthy subjects may have widely different numbers of subpopulations of cells, such as CD3+ T cells) and (ii) it fails to address that pathological samples may have dramatically different cellular composition when compared to healthy samples (e.g. the percent and number of CD3+ T cells in blood are greatly elevated in patients with T cell leukemia over the percent and number in healthy subjects).

For accurate and reproducible staining of cell-containing samples, it may be desirable to add a specific amount of a cellular stain (e.g. DNA dyes, antibodies, binders, etc.) to a specific number or concentration of cells. For example, it may be desirable to add 0.2 micrograms of a particular stain for white blood cells per 1000 white blood cells in a sample. After an incubation period of the dye with the cells, a sample may be washed to remove excess (unbound) dye, prepared to an appropriate cell density for microscopy, and imaged. In this manner, a stain and staining procedure can be optimized or normalized for a particular cell number.

In one embodiment, a method is provided for enumerating the number of cells in a sample. The method may include one or more of the following steps or elements. A first stain that will bind to the cells of interest in a sample may be added to the sample. The mixture of first stain and sample may be incubated. The cells in the mixture of first stain and sample may be washed to remove excess (unbound) stain. The washed cells stained with a first stain may be prepared in a desired volume for further analysis. The washed cells stained with a first stain may be analyzed by a spectrophotometer. Data from the spectrophotometer may be used to enumerate the approximate number of cells in the sample. Based on the number of cells in the sample, a second stain that will bind to cells of interest in a sample may be added to the sample. The mixture of second stain and sample may be incubated. The cells in the mixture of second stain and sample may be washed to remove excess stain. The washed cells stained with a second stain may be prepared in a desired volume for further analysis. The washed cells stained with a second stain may be analyzed by microscopy.

Enumerating Cells in a Sample Prior to Determining the Ploidy of Cells

In one embodiment, a method for enumerating cells in a sample prior to determining the ploidy of the cells is provided, wherein the method includes one or more of the following steps or elements. A first stain which binds to the cells of interest in the sample and that is spectrally distinct from the emission of a DNA dye may be added to the sample. The cells of interest may be, for example, white blood cells. The first stain may be, for example, a fluorphore-conjugated antibody. A fluorphore-conjugated antibody may bind to, for example, a widely expressed antigen (e.g. CD45), or it may bind to an antigen expressed by a specific sub-population of cells (e.g. CD3 for T cells). The mixture of first stain and sample may be incubated. The cells in the mixture of first stain and sample may be washed to remove excess (unbound) stain. The washed cells stained with a first stain may be prepared in a desired volume for further analysis. The washed cells stained with a first stain may be analyzed by a spectrophotometer. Data from the spectrophotometer may be used to enumerate the approximate number of cells in the sample. Based on the number of cells in the sample, a second stain that will bind to cells of interest in a sample may be added to the sample. The second stain may be a DNA dye, such as propidium iodide or 4',6-diamidino-2-phenylindole ("DAPI"). The mixture of second stain and sample may be incubated. The cells in the mixture of second stain and sample may be washed to remove excess stain. The washed cells stained with a second stain may be prepared in a desired volume for further analysis. The washed cells stained with a second stain may be analyzed for ploidy by microscopy.

In methods for determining the ploidy of cells, it may be important to combine a given number of cells for ploidy analysis with a certain amount or concentration of DNA stain, in order to generate accurate and consistent data regarding the ploidy of the cells. In one example, the number of white blood cells per volume of blood may vary within a healthy population, and thus, it may be desirable to determine the number of white blood cells in a volume of blood before attempting to stain the white blood cells for ploidy analysis.

The methods provided above for determining the ploidy of cells may also be performed for any method in which enumerating cells in a sample prior to determining an attribute related to the nucleic acid content of a cell is desired. For example, the above method may be used with methods involving enumerating cells in a sample prior to determining the morphology of nuclei of cells, the size of the nuclei of cells, the ratio of nuclei area to total cell area, etc.

Enumerating Cells in a Sample Prior to Cell Surface Staining

In one embodiment, a method for enumerating cells in a sample prior to cell surface staining is provided, wherein the method includes one or more of the following steps or elements. A first stain which binds to the cells of interest in the sample and that is spectrally distinct from the emission of a dye to be used to stain the surface of the cells of interest may be added to the sample. The cells of interest may be, for example, white blood cells. The first stain may be, for example, a DNA dye (e.g. propidium iodide or DAPI). The mixture of first stain and sample may be incubated. The cells in the mixture of first stain and sample may be washed to remove excess (unbound) stain. The washed cells stained with a first stain may be prepared in a desired volume for further analysis. The washed cells stained with a first stain may be analyzed by a spectrophotometer. Data from the spectrophotometer may be used to enumerate the approximate number of cells in the sample. Based on the number of cells in the sample, a second stain that will bind to cells of interest in a sample may be added to the sample. The second stain may be, for example, a fluorphore-conjugated antibody. A fluorphore-conjugated antibody may bind to, for example, a widely expressed antigen (e.g. CD45), or it may bind to an antigen expressed by a specific sub-population of cells (e.g. CD3 for T cells). The mixture of second stain and sample may be incubated. The cells in the mixture of second stain and sample may be washed to remove excess stain. The washed cells stained with a second stain may be prepared in a desired volume for further analysis. The washed cells stained with a second stain may be analyzed for a cell surface antigen by microscopy.

In methods for cell surface antigen staining of cells, it may be important to combine a given number of cells for analysis with a certain amount or concentration of cell surface antigen stain, in order to generate accurate and consistent data regarding the content of the cell surfaces. In one example, the number of white blood cells per volume of blood may vary within a healthy population, and thus, it may be desirable to determine the number of white blood cells in a volume of blood before attempting to stain the white blood cells for cell surface antigens. In another example, the number of white blood cells per volume of blood may vary between healthy and sick subjects, and thus, it may be desirable to determine the number of white blood cells in a volume of blood before attempting to stain the white blood cells for cell surface antigens. As a theoretical example, a healthy patient may have 100 cells per microliter of blood, and 10 of these are CD3+ T cells, while a lymphoma patient may have 1000 cells per microliter of blood and 900 of these are CD3+ T cells. If 100 microliters of blood is traditionally stained, then a sample from a healthy subject would contain 10,000 total cells/1000 CD3+ T cells, and a sample from a lymphoma subject would contain 100,000 total cells/90,000 CD3+ T cells. In this theoretical example, the pathological sample contains ten times the number of total cells and ninety times the number of CD3+ T cells, when compared to a sample from a healthy subject. If the pathological sample would be stained with a traditional "volumetric staining" approach that is optimized for samples from healthy subjects, the sample from the lymphoma subject may be insufficiently stained.

Accordingly, methods provided herein may be used to enumerate cells in a sample before cell staining, in order to generate accurate and/or consistent data regarding samples.

Method Speeds

Methods, systems, and devices provided herein may support the rapid development of sample analysis results. Any of the methods provided herein may provide analysis results in less than about 6 hours, 4 hours, 3 hours, 2 hours, 1 hour, 45 minutes, 30 minutes, 15 minutes, 10 minutes, or 5 minutes from the initiation of the method.

Rapid analysis results may be used to provide real-time information relevant to the treatment, diagnosis, or monitoring of a patient. For example, rapid analysis results may be used to guide a treatment decision of a surgeon operating on a patient. During surgery, a surgeon may obtain a biological sample from a patient for analysis. By receiving rapid analysis of a sample by a method provided herein, a surgeon may be able to make a treatment decision during the course of surgery.

In another example, rapid analysis results provided by the methods, systems, and devices provided herein may support a patient receiving information regarding a biological sample provided by the patient at a point of service during the same visit to the point of service location in which the patient provided the biological sample.

Analysis of Pathology Samples

Any of the methods provided herein may be used to analyze cell-containing pathology samples. If a pathology sample is a tissue sample, the sample may be treated to separate the cells of the tissue into individual cells for analysis by methods provided herein.

Analysis of pathology samples by any of the methods provided herein may support rapid pathology analysis, and the rapid integration of pathology analysis results into a treatment decision for a patient.

Additional Procedures in Response to Analysis Results

In some embodiments, the devices and systems provided herein may be configured to trigger an additional procedure in response to a result obtained by an analysis method provided herein.

In one example, a device or system may be programmed to provide an alert to a user if a result is outside of an expected range. The alert may prompt a user or medical personnel to, for example, manually analyze a sample, check the device or system for proper operation, etc.

In another example, a device or system may be programmed to automatically run one or more additional tests on a sample if a result is within or outside of a certain range.

In some examples, devices and systems provided herein are capable of performing multiple different assays, and the device or system may run an addition assay to verify or further investigate a result generated by a method provided herein.

Analysis using Non-specific Dyes

One non-limiting example to accelerate imaging is to use a "high light" situation, where cells are labeled with very high concentration of dyes. In the present embodiment, non-specific dyes are used that label the DNA, the membranes, or other portion of the cells. This example does not use anti-body specific dyes.

With the non-specific dye, it is possible to obtain cell information without centrifugation or performing physical separation. Without this separation step, one can more rapidly move directly to imaging the sample, such as but not limited imaging a large area of cells that may include both a) non-target cells such as red blood cells (RBCs) and b) target cells or objects of interest such as white blood cells (WBCs). Thus, in one non-limiting example, one can image five million RBCs and five thousand or other number of WBCs therein. The targeted cells can be differentiated based on what is inside the cell such as but not limited to the shape of nucleus of cell. In one embodiment, this stained the nucleus and based on what a cell has, one can determine cell type based on this, even though the dye is non-specific. In other examples, other internal shapes in the cell such as cytoplasm has granules or other objects therein. For urine sample, it is the cells and crystal shapes that can be used. In this manner, the use of non-specific dyes can be used to rapidly image cells in a manner that can be used to determine cells as desired.

Analysis Using a Plurality of Excitation and/or Detection Channels

In the context of using even smaller sample volumes for cytometry, one thing for advanced cytometry assays is to use additional excitation and/or detection wavelengths. For example, for classification of the lymphocyte subset assay, the various cells such as T cells, B cells, K cells etc . . . are to be counted. In this case, just to identify that the cell is a lymphocyte, one uses two markers. To further sub-classify, one use two markers. If one has a system that can only detect two colors at a time, there is an insufficient number of wavelengths.

In one embodiment, one can aliquot the sample to make two separate samples and image one combination in one part and another combination in another part. Unfortunately, this can cause a doubling of volume and time. The more independent channels one build into our system, the lesser is the number of these sample parts or volume is used.

EXAMPLES

Cell Processing

In embodiments, it is often useful to process biological samples for imaging, testing, and analysis. For example, it is often useful to process biological samples containing cells for imaging, testing, and analysis.

Processing of a biological sample may include pre-processing (e.g., preparation of a sample for a subsequent processing or measurement), processing (e.g., alteration of a sample so that it differs from its original, or previous, state), and post-processing (e.g., disposal of all or a portion of a sample following its measurement or use). A biological sample may be divided into portions, such as aliquots of a blood or urine sample, or such as slicing, mincing, or dividing a tissue sample into two or more pieces. Processing of a biological sample, such as blood sample, may include mixing, stirring, sonication, homogenization, or other processing of a sample or of a portion of the sample. Processing of a biological sample, such as blood sample, may include centrifugation of a sample or a portion thereof. Processing of a biological sample, such as blood sample, may include providing time for components of the sample to separate or settle, and may include filtration (e.g., passing the sample or a portion thereof through a filter). Processing of a biological sample, such as blood sample, may include allowing or causing a blood sample to coagulate. Processing of a biological sample, such as blood sample, may include concentration of the sample, or of a portion of the sample (e.g., by sedimentation or centrifugation of a blood sample, or of a solution containing a homogenate of tissue from a tissue sample) to provide a pellet and a supernatant. Processing of a biological sample, such as blood sample, may include dilution of a portion of the sample. Dilution may be of a sample, or of a portion of a sample, including dilution of a pellet or of a supernatant from sample. A biological sample may be diluted with water, or with a saline solution, such as a buffered saline solution. A biological sample may be diluted with a solution which may or may not include a fixative (e.g., formaldehyde, paraformaldehyde, or other agent which cross-links proteins). A biological sample may be diluted with a solution effective that an osmotic gradient is produced between the surrounding solution and the interior, or an interior compartment, of such cells, effective that the cell volume is altered. For example, where the resulting solution concentration following dilution is less than the effective concentration of the interior of a cell, or of an interior cell compartment, the volume of such a cell will increase (i.e., the cell will swell). A biological sample may be diluted with a solution which may or may not include an osmoticant (such as, for example, glucose, sucrose, or other sugar; salts such as sodium, potassium, ammonium, or other salt; or other osmotically active compound or ingredient). In embodiments, an osmoticant may be effective to maintain the integrity of cells in the sample, by, for example, stabilizing or reducing possible osmotic gradients between the surrounding solution and the interior, or an interior compartment, of such cells. In embodiments, an osmoticant may be effective to provide or to increase osmotic gradients between the surrounding solution and the interior, or an interior compartment, of such cells, effective that the cells at least partially collapse (where the cellular interior or an interior compartment is less concentrated than the surrounding solution), or effective that the cells swell (where the cellular interior or an interior compartment is more concentrated than the surrounding solution).

A biological sample may be dyed, or markers may be added to the sample, or the sample may be otherwise prepared for detection, visualization, or quantification of the sample, a portion of a sample, a component part of a sample, or a portion of a cell or structure within a sample. For example, a biological sample may be contacted with a solution containing a dye. A dye may stain or otherwise make visible a cell, or a portion of a cell, or a material or molecule associated with a cell in a sample. A dye may bind to or be altered by an element, compound, or other component of a sample; for example a dye may change color, or otherwise alter one of more of its properties, including its optical properties, in response to a change or differential in the pH of a solution in which it is present; a dye may change color, or otherwise alter one of more of its properties, including its optical properties, in response to a change or differential in the concentration of an element or compound (e.g., sodium, calcium, CO2, glucose, or other ion, element, or compound) present in a solution in which the dye is present. For example, a biological sample may be contacted with a solution containing an antibody or an antibody fragment. For example, a biological sample may be contacted with a solution that includes particles. Particles added to a biological sample may serve as standards (e.g., may serve as size standards, where the size or size distribution of the particles is known, or as concentration standards, where the number, amount, or concentration of the particles is known), or may serve as markers (e.g., where the particles bind or adhere to particular cells or types of cells, to particular cell markers or cellular compartments, or where the particles bind to all cells in a sample).

Cytometry includes observations and measurements of cells, such as red blood cells, platelets, white blood cells, including qualitative and quantitative observations and measurements of cell numbers, cell types, cell surface markers, internal cellular markers, and other characteristics of cells of interest. Where a biological sample includes or is a blood sample, the sample may be divided into portions, and may be diluted (e.g., to provide greater volume for ease of handling, to alter the density or concentration of cellular components in the sample to provide a desired diluted density, concentration, or cell number or range of these, etc.). The sample may be treated with agents which affect coagulation, or may be treated or handled so as to concentrate or precipitate sample components (e.g., ethylene diamine tetraacetic acid (EDTA) or heparin may be added to the sample, or the sample may be centrifuged or cells allowed to settle). A sample, or portion of a sample, may be treated by adding dyes or other reagents which may react with and mark particular cells or particular cellular components. For example, dyes which mark cell nuclei (e.g., hematoxylin dyes, cyanine dyes, drag dyes such as Draq5, and others); dyes which mark cell cytoplasm (e.g., eosin dyes, including fluorescein dyes, and others) may be used separately or together to aid in visualization, identification, and quantification of cells. More specific markers, including antibodies and antibody fragments specific for cellular targets, such as cell surface proteins, intracellular proteins and compartments, and other targets, are also useful in cytometry.

Biological samples may be measured and analyzed by cytometry using optical means, including, for example, photodiode detectors, photomultipliers, charge-coupled devices, laser diodes, spectrophotometers, cameras, microscopes, or other devices which measure light intensity (of a single wavelength, of multiple wavelengths, or of a range, or ranges, of wavelengths of light), form an image, or both. A field of view including a sample, or portion of a sample, may be imaged, or may be scanned, or both, using such detectors. A biological sample may be measured and analyzed by cytometry prior to processing, dilution, separation, centrifugation, coagulation, or other alteration. A biological sample may be measured and analyzed by cytometry during or following processing, dilution, separation, centrifugation, coagulation, or other alteration of the sample. For example, a biological sample may be measured and analyzed by cytometry directly following receipt of the sample. In other examples, a biological sample may be measured and analyzed by cytometry during or after processing, dilution, separation, centrifugation, coagulation, or other alteration of the sample.

For example, a blood sample or portion thereof may be prepared for cytometry by sedimentation or centrifugation. A sedimented or pellet portion of such a sample may be resuspended in a buffer of choice prior to cytometric analysis (e.g., by aspiration, stirring, sonication, or other processing). A biological sample may be diluted or resuspended with water, or with a saline solution, such as a buffered saline solution prior to cytometric analysis. A solution used for such dilution or resuspension may or may not include a fixative (e.g., formaldehyde, paraformaldehyde, or other agent which cross-links proteins). A solution used for such dilution or resuspension may provide an osmotic gradient between the surrounding solution and the interior, or an interior compartment, of cells in the sample, effective that the cell volume of some or all cells in the sample is altered. For example, where the resulting solution concentration following dilution is less than the effective concentration of the interior of a cell, or of an interior cell compartment, the volume of such a cell will increase (i.e., the cell will swell). A biological sample may be diluted with a solution which may or may not include an osmoticant (such as, for example, glucose, sucrose, or other sugar; salts such as sodium, potassium, ammonium, or other salt; or other osmotically active compound or ingredient). In embodiments, an osmoticant may be effective to maintain the integrity of cells in the sample, by, for example, stabilizing or reducing possible osmotic gradients between the surrounding solution and the interior, or an interior compartment, of such cells. In embodiments, an osmoticant may be effective to provide or to increase osmotic gradients between the surrounding solution and the interior, or an interior compartment, of such cells, effective that the cells at least partially collapse (where the cellular interior or an interior compartment is less concentrated than the surrounding solution), or effective that the cells swell (where the cellular interior or an interior compartment is more concentrated than the surrounding solution).

For example, a biological sample may be measured or analyzed following dilution of a portion of the sample with a solution including dyes. For example, a biological sample may be measured or analyzed following dilution of a portion of the sample with a solution including antibodies or antibody fragments. For example, a biological sample may be measured or analyzed following dilution of a portion of the sample with a solution including particles. Particles added to a biological sample may serve as standards (e.g., may serve as size standards, where the size or size distribution of the particles is known, or as concentration standards, where the number, amount, or concentration of the particles is known), or may serve as markers (e.g., where the particles bind or adhere to particular cells or types of cells, to particular cell markers or cellular compartments, or where the particles bind to all cells in a sample).

For example, a biological sample may be measured or analyzed following processing which may separate one or more types of cells from another cell type or types. Such separation may be accomplished by gravity (e.g., sedimentation); centrifugation; filtration; contact with a substrate (e.g., a surface, such as a wall or a bead, containing antibodies, lectins, or other components which may bind or adhere to one cell type in preference to another cell type); or other means. Separation may be aided or accomplished by alteration of a cell type or types. For example, a solution may be added to a biological sample, such as a blood sample, which causes some or all cells in the sample to swell. Where one type of cell swells faster than another type or types of cell, cell types may be differentiated by observing or measuring the sample following addition of the solution. Such observations and measurements may be made at a time, or at multiple times, selected so as to accentuate the differences in response (e.g., size, volume, internal concentration, or other property affected by such swelling) and so to increase the sensitivity and accuracy of the observations and measurements. In some instances, a type or types of cells may burst in response to such swelling, allowing for improved observations and measurements of the remaining cell type or types in the sample.

Observation, measurement and analysis of a biological sample by cytometry may include photometric measurements, for example, using a photodiode, a photomultiplier, a laser diode, a spectrophotometer, a charge-coupled device, a camera, a microscope, or other means or device. Cytometry may include preparing and analyzing images of cells in a biological sample (e.g., two-dimensional images), where the cells are labeled (e.g., with fluorescent, chemiluminescent, enzymatic, or other labels) and plated (e.g., allowed to settle on a substrate) and imaged by a camera. The camera may include a lens, and may be attached to or used in conjunction with a microscope. Cells may be identified in the two-dimensional images by their attached labels (e.g., from light emitted by the labels).

An image of cells prepared and analyzed by a cytometer as disclosed herein may include no cells, one cell, or multiple cells. A cell or cell in an image of a cytometer, as disclosed herein, may be labeled, as disclosed above. A cell or cell in an image of a cytometer, as disclosed herein, may be labeled, as disclosed above, effective to identify the image, and the subject from whom the sample was taken.

In some embodiments, the assay system is configured to perform cytometry assays. Cytometry assays are typically used to optically, electrically, or acoustically measure characteristics of individual cells. For the purposes of this disclosure, "cells" may encompass non-cellular samples that are generally of similar sizes to individual cells, including but not limited to vesicles (such as liposomes), small groups of cells, virions, bacteria, protozoa, crystals, bodies formed by aggregation of lipids and/or proteins, and substances bound to small particles such as beads or microspheres. Such characteristics include but are not limited to size; shape; granularity; light scattering pattern (or optical indicatrix); whether the cell membrane is intact; concentration, morphology and spatio-temporal distribution of internal cell contents, including but not limited to protein content, protein modifications, nucleic acid content, nucleic acid modifications, organelle content, nucleus structure, nucleus content, internal cell structure, contents of internal vesicles (including pH), ion concentrations, and presence of other small molecules such as steroids or drugs; and cell surface (both cellular membrane and cell wall) markers including proteins, lipids, carbohydrates, and modifications thereof. By using appropriate dyes, stains, or other labeling molecules either in pure form, conjugated with other molecules or immobilized in, or bound to nano- or micro-particles, cytometry may be used to determine the presence, quantity, and/or modifications of specific proteins, nucleic acids, lipids, carbohydrates, or other molecules. Properties that may be measured by cytometry also include measures of cellular function or activity, including but not limited to phagocytosis, antigen presentation, cytokine secretion, changes in expression of internal and surface molecules, binding to other molecules or cells or substrates, active transport of small molecules, mitosis or meiosis; protein translation, gene transcription, DNA replication, DNA repair, protein secretion, apoptosis, chemotaxis, mobility, adhesion, antioxidizing activity, RNAi, protein or nucleic acid degradation, drug responses, infectiousness, and the activity of specific pathways or enzymes. Cytometry may also be used to determine information about a population of cells, including but not limited to cell counts, percent of total population, and variation in the sample population for any of the characteristics described above. The assays described herein may be used to measure one or more of the above characteristics for each cell, which may be advantageous to determine correlations or other relationships between different characteristics. The assays described herein may also be used to independently measure multiple populations of cells, for example by labeling a mixed cell population with antibodies specific for different cell lines. A microscopy module may permit the performance of histology, pathology, and/or morphological analysis with the device, and also facilitates the evaluation of objects based on both physical and chemical characteristics. Tissues can be homogenized, washed, deposited on a cuvette or slide, dried, stained (such as with antibodies), incubated and then imaged. When combined with the data transmission technologies described elsewhere herein, these innovations facilitate the transmission of images from a CMOS/CDD or similar detector to, e.g., a licensed pathologist for review, which is not possible with traditional devices that only perform flow cytometry. The cytometer can measure surface antigens as well as cell morphology; surface antigens enable more sensitive and specific testing compared to traditional hematology laboratory devices. The interpretation of cellular assays may be automated by gating of one or more measurements; the gating thresholds may be set by an expert and/or learned based on statistical methods from training data; gating rules can be specific for individual subjects and/or populations of subjects.

In some embodiments, the incorporation of a cytometer module into a point of service device provides the measurement of cellular attributes typically measured by common laboratory devices and laboratories for interpretation and review by classically-trained medical personnel, improving the speed and/or quality of clinical decision-making. A point of service device may, therefore, be configured for cytometric analysis.

Example 1

A sample of cells containing blood leukocytes including natural killer cells and neutrophils was obtained. The sample was treated with a fluorescently labeled identity binder (anti-CD16 binder), which binds to both natural killer cells and neutrophils. The sample was also treated with a nuclear dye (DRAQ5). The sample was imaged by fluorescence microscopy and dark field microscopy. The level of fluorescence and light side scatter of different cells in the sample was recorded and analyzed. Segmented images containing the anti-CD16 binder signal provided quantitative information on the fluorescence intensity of each cell (corresponding to the CD16 expression level), and also the size of each cell. The darkfield image provided quantitative information on the scatter properties of each cell. Images containing the DNA dye signal were segmented to determine the fluorescent intensity, size, and shape of the nucleus.

Figure 1B:
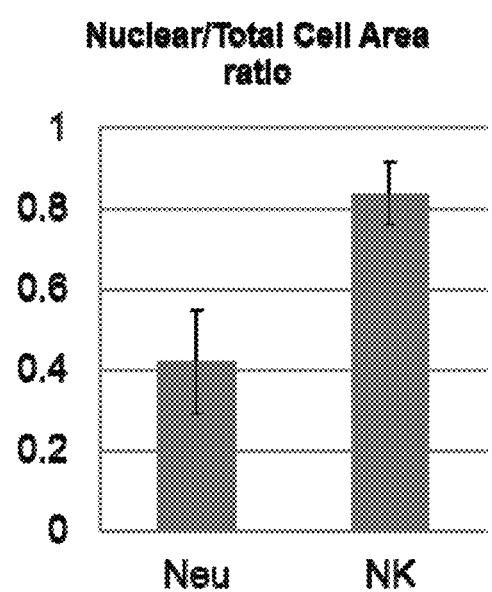
FIG. 1B shows a bar graph showing the ratio of nuclear area to total cell area of natural killer cells ("NK") and neutrophils ("Neu").
Figure 1C:
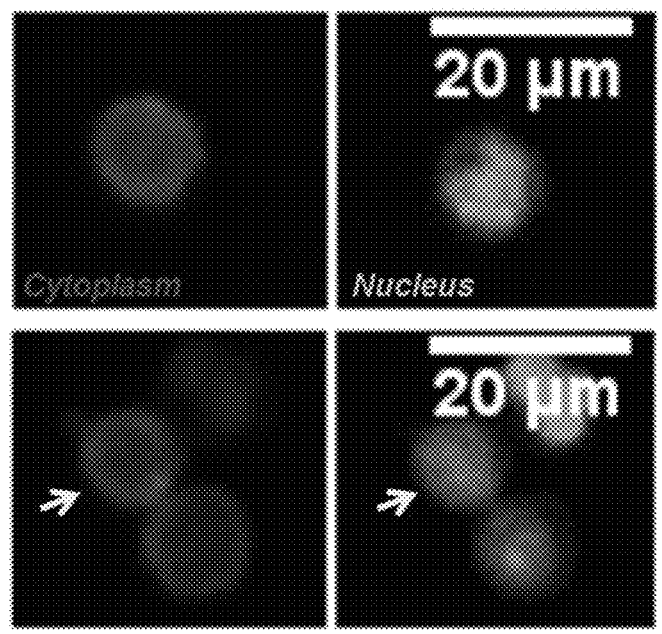
FIG. 1C shows natural killer cells stained with anti-CD16 antibody (left column) and a nuclear stain (right column).
Figure 1D:
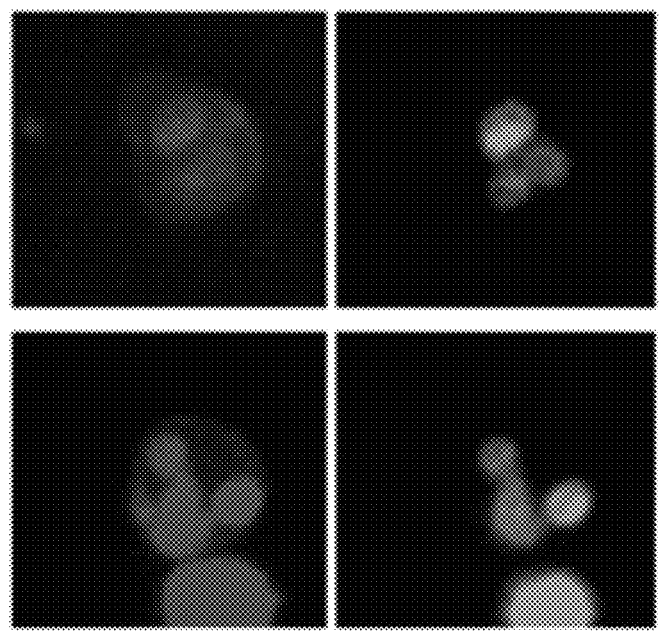
FIG. 1D shows neutrophils stained with anti-CD16 antibody (left column) and a nuclear stain (right column).

As shown in FIG. 1A, two major groupings cells were identified based on the measurement of CD16 fluorescence and light scatter of the different cells. The group of cells with bright/high CD16 fluorescence signal and high scatter (FIG. 1A, right circle) are neutrophils. The group of cells with intermediate CD16 fluorescence signal and low scatter (FIG. 1A, left circle) are natural killer cells. While the measurement of fluorescence and light scatter of the different cells provides enough information to classify most cells in the sample as either natural killer cells or neutrophils, for some cells, measurement of these attributes does not provide enough information to classify the cells with a high degree of accuracy. For example, the measurement of fluorescence and light scatter of cells does not provide enough information to accurately classify the small group of cells in the smallest circle in FIG. 1A (i.e. the middle circle). In order to identify whether the cells in the smallest circle were natural killer cells or neutrophils, images of the nuclear (DRAQ5) and total cell (anti-CD16) staining of these were examined. Quantitative measurements of the area of the nucleus and the total cell volume of the cells were obtained, and the ratio of nuclear area to total cell area was determined. As shown in FIG. 1B, there is a clear difference in the ratio of nuclear area to total cell area between natural killer cells ("NK") and neutrophils ("Neu"). Thus, the use of quantitative microscopy to examine multiple attributes of cells in the sample was used to allow for unambiguous classification of cells. FIG. 1C shows images of natural killer cells from the smallest circle in FIG. 1A. All images have the same length scale. The images on the left are cells stained for total cell area (anti-CD16), and the images on the right are the same cells with just nuclear staining (DRAQ5). The images on the top and bottom row are different examples of the natural killer cells. FIG. 1D shows images of neutrophils from the smallest circle in FIG. 1A. All images have the same length scale. The images on the left are cells stained for total cell area, and the images on the right are the same cells with just nuclear staining. The images on the top and bottom row are different examples of the natural killer cells.

In addition, the nucleus of a neutrophil has a distinctive multi-lobed shape, whereas the nucleus of a natural killer cell (and other lymphocytes) is round, even, and smooth. Image segmentation algorithms may be used to identify and classify cells based on the shape of the nucleus itself.

Example 2

Figure 2A:
FIG. 2A shows platelets labeled with fluorescently conjugated CD41 and CD61 antibodies (bright dots).
Figure 2B:
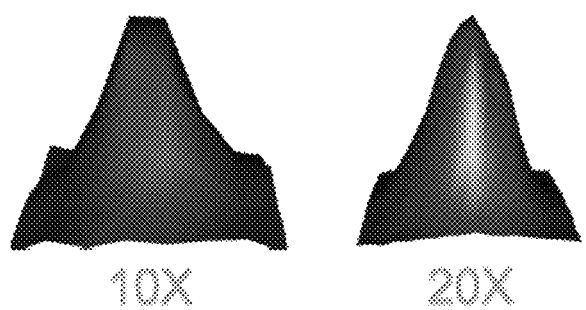
FIG. 2B shows the intensity distribution of images of fluorescently labeled platelets at 10× (left) and 20× (right) magnification.
Figure 2C:
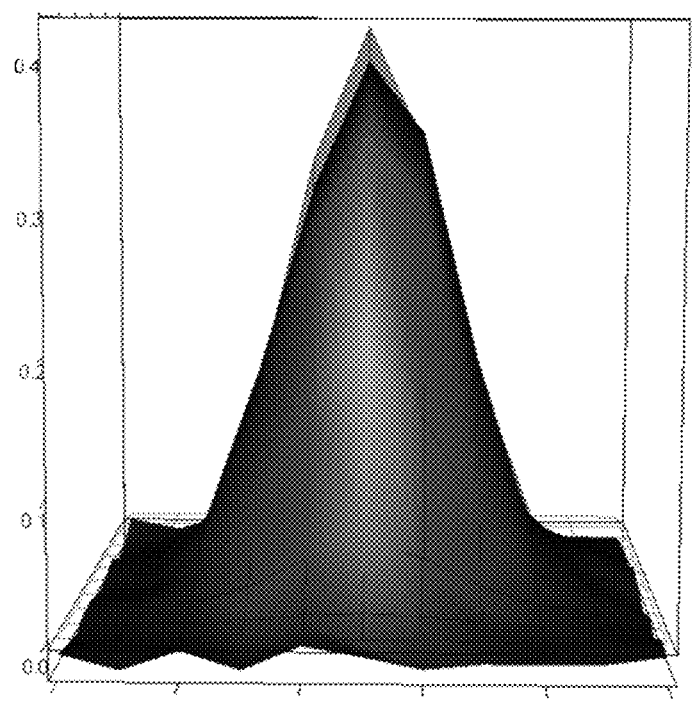
FIG. 2C shows the intensity distribution of an image of a fluorescently labeled platelet showing measured intensity (light grey) and curve fit to the measured intensity (dark grey).

A sample containing platelets was obtained. The platelets were labeled with fluorescently conjugated anti-CD41 and anti-CD61 antibodies. Beads having a diameter of 3 μm were also added to the sample. The sample was imaged at 10× and 20× magnifications (FIG. 2A). The intensity of fluorescence distribution for individual platelets was measured (from both antibodies), and determined have a Gaussian shape (FIG. 2B). The measured values of fluorescence of individual platelets was plotted, and a fit for the intensity distribution was determined (FIG. 2C). In FIG. 2C, the grey line is the measured fluorescence intensity across an individual platelet, and the black line is the fit. Parameters of the fit, such as the mean of the Gaussian, the variance, the volume, the width, and the area of the base, etc., can be evaluated as predictors of platelet volume. The volume of the Gaussian and the width of the fit have been determined to correlate closely with mean platelet volume.

For the above measurements, the 3 μm beads served as references and fiducials for controlling variance in accurately determining the best plane of focus, and the effect of this variance on the measurement of volume.

Figure 3:
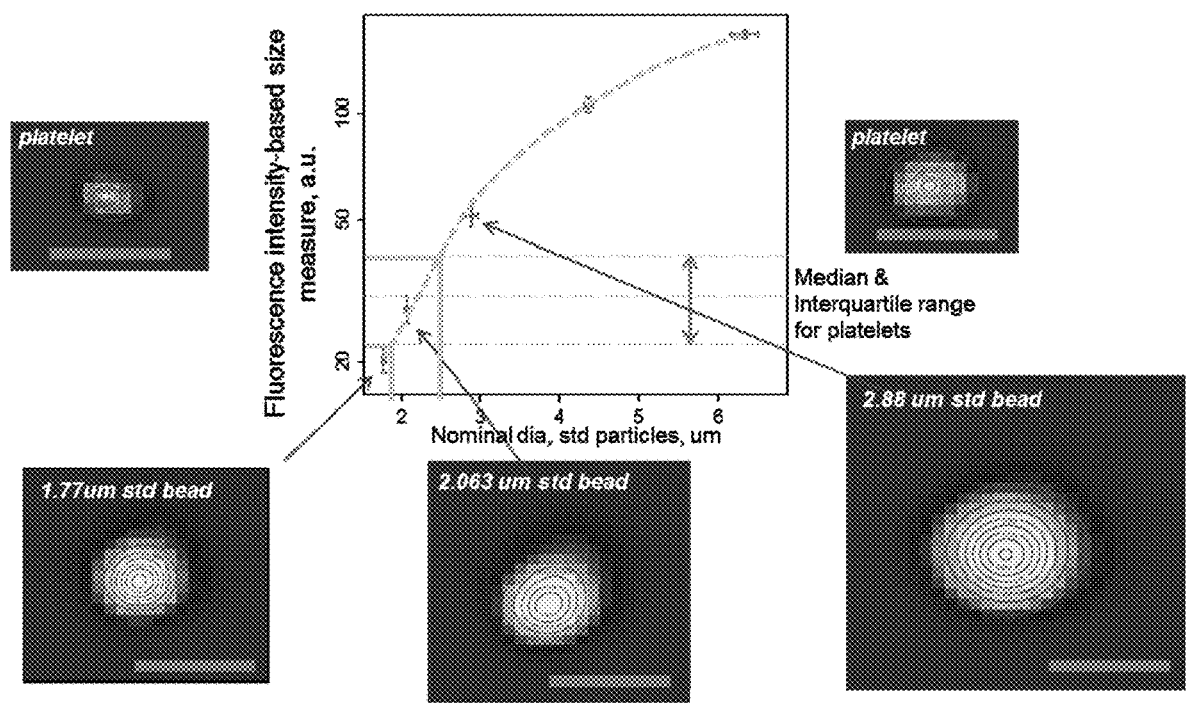
FIG. 3 shows a plot of a curve of showing the relationship between the nominal diameter of standard particles in μm (x-axis) and fluorescence intensity-based size as measured in arbitrary units (a.u.) (y-axis). The figure also shows representative beads at different points along the curve.

In addition, platelet size estimated based on fitting a 2D model can be calibrated to be in the normal range (FIG. 3).

Example 3

Figure 4A:
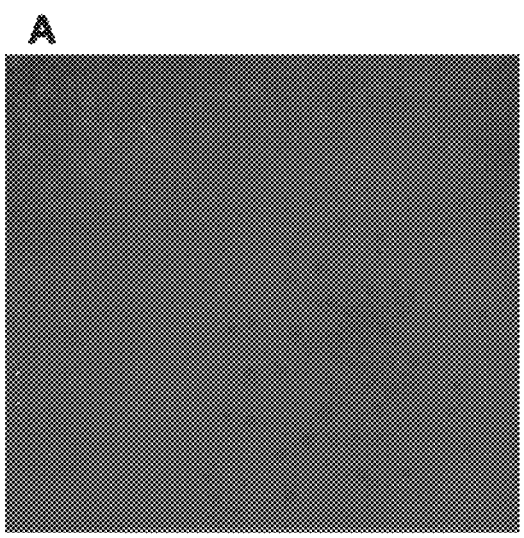
FIG. 4A shows sphered red blood cells imaged by dark field microscopy in cuvettes that allow only epi-illumination.
Figure 4B:
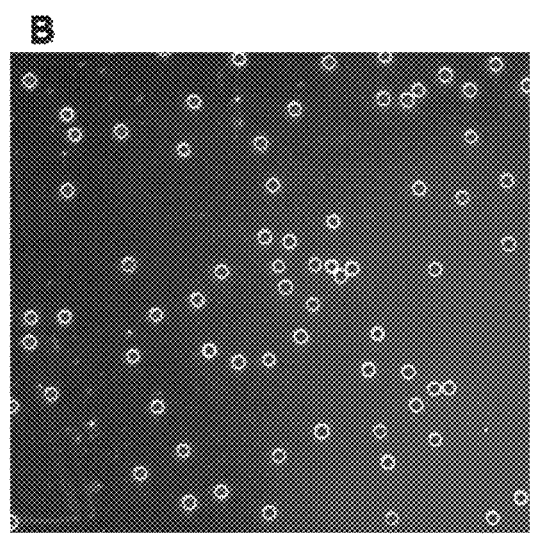
FIG. 4B shows sphered red blood cells imaged by dark field microscopy in cuvettes that allow a mixture of epi- and trans-illumination.

A sample containing red blood cells ("RBCs") was obtained. The RBCs were treated to swell the RBCs into a sphere-like shape, by treating the RBCs with a low concentration of a surfactant (DDAPS or SDS). The RBCs were imaged by dark field microscopy in two different cuvettes: (A) a cuvette that allowed only pure epi-illumination (FIG. 4A); and (B) a cuvette that allowed a mixture of both epi and trans-illumination (FIG. 4B). The RBCs were much more visible in the cuvette that allowed a mixture of both epi and trans-illumination over the cuvette that allowed only pure epi-illumination (FIG. 4).

Example 4

A sample containing neutrophils was obtained. In neutrophils, the shape and chromatin morphology of the nucleus may indicate whether it is an immature "band" neutrophil or a mature "segmented" neutrophil. Band neutrophils are immature neutrophils that have recently emerged from the bone marrow. An increase in the proportion of band neutrophils may indicate an ongoing infection or inflammation.

The sample was mixed with a fluorescently labeled anti-CD16 antibody, which recognizes CD16, a cell surface receptor on neutrophils. The sample was also stained with a fluorescent nuclear dye. The sample was imaged by fluorescence microscopy, to obtain both nuclear staining and CD16 staining data from the cells. Band neutrophils generally have similar expression levels of CD16 as mature segmented neutrophils, and thus cannot be distinguished by virtue of fluorescence intensity from CD16 staining alone.

Figure 5A:
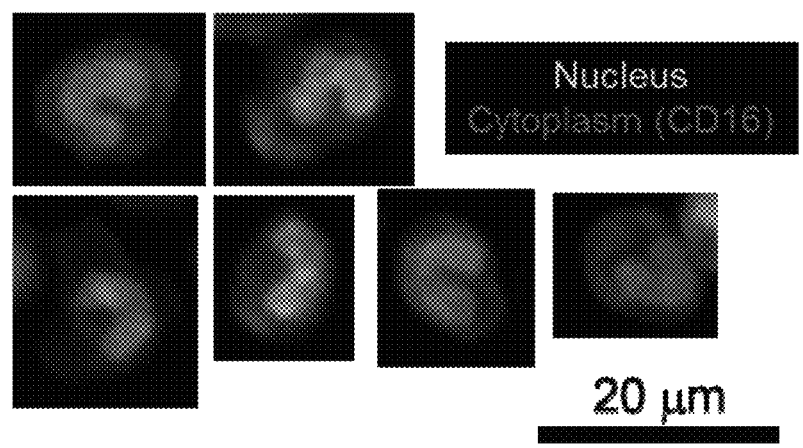
FIG. 5A shows putative band neutrophils stained with anti-CD16 antibody and a nuclear stain.
Figure 5B:
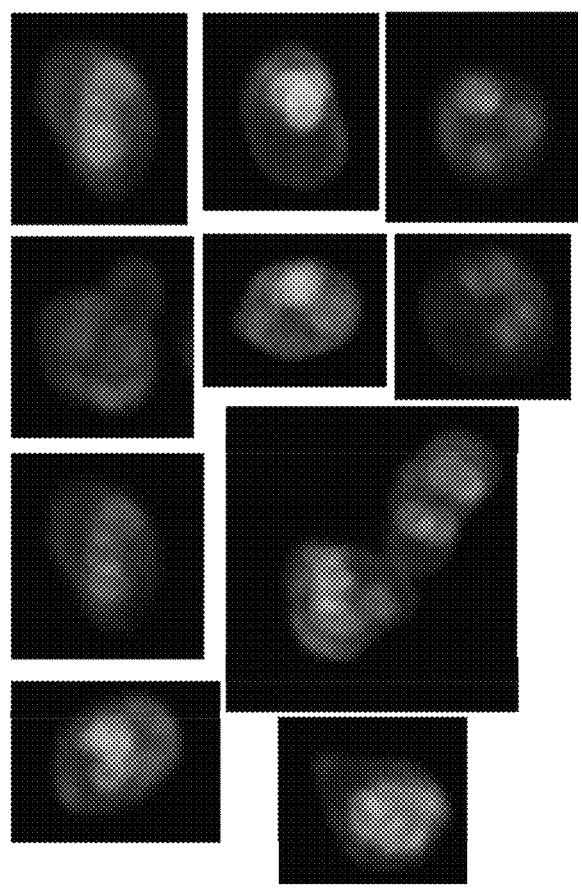
FIG. 5B shows putative segmented neutrophils stained with anti-CD16 antibody and a nuclear stain.

Image analysis including image segmentation is used to recognize nuclear staining and morphologies of band neutrophils and segmented neutrophils, thereby allowing classification of the cells. The size, shape, and fluorescence intensity of the nucleus of cells are examined. In addition, the nuclei are analyzed to determine the number of lobes (peaks in intensity within the nuclear area), distance between the lobes of the nucleus, and the changes in curvature (second derivative) of the nuclear outline. FIG. 5A shows representative images of band neutrophils. In these images, the nucleus appears as a light grey, and the cell cytoplasm appears as a darker grey. As neutrophils differentiate through the myeloid lineage, they develop a characteristic "U" shaped nucleus prior to reaching full maturity. FIG. 5B shows representative images of segmented neutrophils. In these images, the nucleus appears as a light grey, and the cell cytoplasm appears as a darker grey. The nuclei of segmented neutrophils have multiple segments/lobes (typically about 3-5). Thus, this analysis supports identification and quantification of different subpopulations of neutrophils in the blood.

Example 5

A sample of cells from a subject with chronic lymphocytic leukemia (CLL) is obtained. The objective is to quantify the extent of CD5 expression on B-cells from the subject. Anti-CD20 antibodies are selected as the binder for B-cells. Anti-CD20 antibodies labeled with a first colored fluorphore are mixed with the sample. After an appropriate incubation time, the sample is washed and the unbound anti-CD20 antibodies are removed. The sample is exposed to a light source capable of exciting the first fluorophore, and fluorescent signal is measured using a spectrophotometer. Based on the fluorescent signal, the approximate concentration of B-cells in the sample is determined. The determined approximate concentration of B-cells is, in fact, within 1.5 fold of the true concentration of B-cells in the sample.

Based on the approximate concentration of B-cells in the sample, an appropriate amount of anti-CD5 binder is added to the sample so that a proportional relationship between CD5 expression and CD5 fluorescence is maintained. The anti-CD5 binder is coupled to a second fluorophore, which has a different peak excitation wavelength than the first fluorophore (attached to the anti-CD20 binder). The anti-CD5 antibody is added to the sample, and then individual cells of the sample are exposed to a light source capable of exciting the second fluorophore, and fluorescent signal from individual cells is measured. Based on the fluorescent signal from cells, the average amount of CD5 in B-cells in the sample is determined.

Although this example it described in the context of CD5, it should be understood that this concept of obtaining an approximate count to guide in addition of a desire amount of material for use in a subsequent step, is not limited to CD5 and use of this concept with other types of cells, analytes, or objects is not excluded.

Example 6

Blood cells may be imaged, identified, and quantified according to the methods disclosed herein. For example, two-dimensional images of cells in a biological sample, where the cells are labeled (e.g., with fluorescent, chemiluminescent, enzymatic, or other labels) and plated (e.g., allowed to settle on a substrate) and imaged by a camera, may be prepared and analyzed as described in the present example. The camera may include a lens, and may be attached to or used in conjunction with a microscope. Cells may be identified in the two-dimensional images by their attached labels (e.g., from light emitted by the labels).

80 microliters of whole blood obtained from a fingerstick was loaded into a capped vessel preloaded with 2 mg/ml EDTA. The capped vessel was centrifuged at 1200×g for 5 minutes, to separate the blood cells from the blood plasma. Centrifugation of the capped vessel resulted in the separation of the blood sample in the capped vessel into two major components (from top of the capped vessel to the bottom): 1) blood plasma and 2) packed blood cells. This process ensures that no droplets of blood remain isolated, but coalesce with the main body of the liquid. In addition, this process separates the cells from elements of the plasma thus reducing metabolism and allowing for longer storage of the sample.

The centrifuged capped vessel was loaded into a cartridge containing multiple fluidically isolated reagents, tips, and a cytometry cuvette. The cartridge contained all the reagents required for the assay. The cartridge was loaded into a device equipped with at least a centrifuge, a pipette and a platform to load the cuvette. The pipette in the device has a plurality of nozzles, some nozzles being of a different size than some other nozzles.

Inside the device, a nozzle on the pipette was lowered on a cuvette carrier tool causing it to engage a corresponding hole on the carrier tool. This tool was subsequently moved to the cartridge and lowered on the cytometer cuvette. Pins on the tool were then able to engage corresponding holes on the cuvette and pick it up. The cuvette was transferred to a loading station elsewhere in the device.

Next, inside the device, a larger nozzle of the pipette was lowered into the cartridge to engage a pipette tip stored in the cartridge. The pipette and tip together were then used to mix the cells and plasma in the capped vessel by positioning the pipette tip within the sample in the capped vessel and repeatedly aspirating material into and dispensing material from the tip. Once the cells were resuspended in the plasma so that the whole blood sample was thoroughly mixed, 5 microliters of the mixed whole blood was aspirated to provide an aliquot for measurements of properties of the blood sample. This 5 microliter aliquot was used for measurements directed to the red blood cells and platelets in the sample. As discussed below, a portion of the sample remaining after removal of this 5 microliter aliquot was used for measurements directed at white blood cells in the sample.

The 5 microliters of whole blood was dispensed into a vessel containing a mixture of phosphate buffered saline and 2% by weight of bovine serum albumin, to dilute the whole blood twenty-fold (resulting in 100 microliters of diluted sample). After mixing vigorously, 5 microliters of this sample was transferred to another vessel containing a cocktail of labeling antibody reagents: anti-CD235a conjugated to alexa-fluor 647 (AF647), anti-CD41 and anti-CD61 conjugated to phycoerythrin (PE). The mixture was incubated for 5 minutes. Subsequently, 10 microliters of this mixture was mixed with 90 microliters of a buffer containing a zwitterionic surfactant at <0.1% by weight. The surfactant molecules modify bending properties of the red cell membrane such that all cells assume a stable spherical shape. This transformation is isovolumetric as the buffer used is isotonic with cytoplasm and no exchange of fluid can occur across the cell membrane. After incubating this for another 2 minutes, 30 microliters of this solution was mixed with a solution containing glutaraldehyde, a fixative and non-fluorescent beads of 10 um diameter. The mixture had a final concentration of 0.1% glutaraldehyde and 1000 beads per microliter. Glutaraldehyde rapidly fixes cells thus preventing cell lysis and other active biological processes.

In this non-limiting example, the pipette then engaged a tip in the cartridge, aspirated 7 microliters of the above mixture of and loaded the 7 microliters into a channel within the cuvette placed on a platform with the carrier tool. After the mixture was loaded in into cuvette, the pipette aspirated 10 microliters of mineral oil from a vessel in the cartridge, and placed a drop of mineral oil on both open ends of the loaded channel of the cuvette. Mineral oil was added to the ends of the open channel to prevent evaporation of liquid from the loaded cuvette channel. Next, the device-level sample handling apparatus engaged the cuvette carrier/cuvette combination, and transported the cuvette carrier/cuvette combination from the module containing the cartridge to the cytometry module of the device. At the cytometry module, the device-level sample handling apparatus placed the cuvette carrier/cuvette combination on the microscopy stage of the cytometry module. The time required for these operations, in addition to a 2 minute wait time allowed the swollen cells to settle to the floor of the cuvette prior to imaging.

After the cuvette carrier/cuvette was placed on the microscopy stage, the stage was moved to pre-determined location so that the optical system of the cytometer could view one end of the channel containing the sample. At this location, the optical system relayed images of the sample acquired with darkfield illumination from a ringlight. These images coupled with actuation of the optical system on an axis perpendicular to the plane of the cuvette were used to find the plane of best focus. Once focused, the optical system was used to acquire fluorescence images of the sample at different wavelengths, commensurate with the fluorophores that were being used. For example, to visualize red blood cells that had been labeled with anti-CD235 conjugated to alexa fluor 647, a red (630 nm wavelength) light source was used to excite the sample and wavelengths between 650 nm and 700 nm were used to image the sample. A combination of a polychroic mirror and a bandpass emission filter was used to filter out unwanted wavelengths from the optical signal. Since the cells had settled on the floor of the cuvette, images at a single plane of focus were sufficient to visualize all cells in the region.

Data from the images was processed by a controller associated with the sample processing device. The image processing algorithms employed here utilized fluorescence images of cells to detect them using a combination of adaptive thresholding and edge detection. Based on local intensity and intensity gradients, regions of interest (RoI) were created around each cell. Using darkfield images, beads in the sample were also identified and RoIs were created around the beads. All the RoIs in each field of view were enumerated and their intensity in each image of that field of view were calculated. The information output by the image processing algorithm consisted of shape or morphometric measurements and fluorescence and darkfield intensities for each RoI. This information was analyzed using statistical methods to classify each object as either a red blood cell (positive for CD235a, but negative for CD41/CD61), a platelet (positive for CD41/CD61 and negative CD235a) or a bead. The shape descriptors such as perimeter, diameter and circularity were used to calculate the volume of each red blood cell and platelet. Since the beads were added at a known concentration, the average ratio of beads to cells over the whole channel was used to calculate cell concentration in terms of cells/microliter. Based on the steps performed for processing the sample, this concentration was corrected for dilution to arrive at concentration of cells in the original whole blood sample. The following quantities were calculated from a sample: 1) number of red blood cells in the cuvette; 2) average volume of red blood cells in the cuvette; 3) red blood cell distribution width (RDW) of red blood cells in the cuvette; 4) number of platelets in the cuvette; and 5) average volume of platelets in the cuvette. Based on these calculations, the following was calculated for the original blood sample.

| Measured Value | Result | Exemplary Range |
|---|---|---|
| Concentration of red blood cells (million cells per microliter) | 4.8 | 4-6 |
| Mean volume of red blood cells, femtoliter | 88 | 80-100 |
| red blood cell distribution width (RDW), (%) | 12 | 11-14.6 |
| Concentration of platelets (thousand cells per microliter) | 254 | 150-400 |
| Mean volume of platelets, femtoliter | 10.4 | 7.5-11.5 |

After removal of the 5 microliter aliquot used for analysis of RBC and platelet information, the remaining 75 microliters of sample was used to analyze the white blood cell population of the whole blood sample. The remaining 75 microliters of whole blood had also been mixed by repeatedly aspirating and dispensing the sample within the same the vessel by the pipette. Approximately 40 microliters of the remaining 75 microliters of mixed whole blood was aspirated into a pipette tip, and transferred by the pipette to a centrifuge tube in the cartridge. The centrifuge tube containing the blood sample was engaged by the pipette, and transferred to and deposited in a swinging bucket in a centrifuge within the module. The centrifuge was spun to provide 1200×g for 3 minutes, separating the blood into EDTA-containing plasma as the supernatant and packed cells in the pellet.

After centrifugation, the centrifuge tube was removed from the centrifuge and returned to the cartridge. The plasma supernatant was removed by the pipette and transferred to a separate reaction vessel in the cartridge. From a reagent vessel in the cartridge, 16 microliters of resuspension buffer was aspirated by the pipette, and added to the cell pellet in the centrifuge tube. The pipette then resuspended the cell pellet in the resuspension buffer by repeatedly aspirating and dispensing the mixture in the centrifuge tube. Next, the pipette aspirated 21 microliters of the resuspended whole blood and added it to another vessel containing 2 microliters of anti CD14-pacific blue and draq5, mixed, and incubated for 2 minutes. Twenty microliters of this mixture was then added to 80 microliters of a lysis buffer. The lysis buffer is a solution of a gentle surfactant such a saponin in conjunction with a fixative such as paraformaldehyde. The detergent causes a large number of holes to be formed in the membranes of cells. Red blood cells, due to their unique membrane properties, are particularly susceptible to this hole formation and lyse completely, their contents leaking out into the liquid around. Presence of the fixative prevents unintentional lysis of the white blood cells. Platelets also remain unlysed. The purpose of this step is to remove red blood cells from the mixture as they outnumber white blood cells by about 1000:1. Platelets do not interfere with imaging and hence are irrelevant to this process. The lysis buffer also contained 10 μM non-fluorescent beads at a known concentration.

After a 5 minute incubation, the vessel was spun again at 1200×g for 3 minutes. The supernatant was aspirated by a pipette tip, removing the red blood cell ghosts and other debris, and deposited into a waste area in the cartridge. Approximately 15 microliters of liquid with packed white blood cells were present in the cell pellet.

In order to determine a rough approximation of the number of white blood cells present in the cell pellet, the pipette first resuspended the white blood cells in the vessel and then aspirated the liquid, transferred it to spectrophotometer in the blade The white blood cell suspension was illuminated with light at a wavelength of 632 nm, which is the excitation wavelength for alexa fluor 647 dye and draq5. The light emitted by the cell suspension was filtered by a 650 nm long pass filter and measured in the spectrophotometer. This measurement was correlated with previously generated calibration curve to estimate a rough concentration of white blood cells in the cell suspension. Typically, cell concentrations ranged from about 1000 cells per microliter to about 100,000 cells per microliter. This estimate was used to calculate an appropriate dilution factor to ensure that the concentration of cells in the cuvette was constrained to within a two-fold range around a pre-defined target concentration. The purpose of this step was to ensure that cells are not present at too high or too low a density on the cuvette. If the cell density is too high, the accuracy of image processing algorithms is compromised, and if the cell density is too low, an insufficient number of cells are sampled.

Based on the dilution factor calculated in the above step, a diluent containing labeled antibodies against CD45 (pan-leukocyte marker), CD16 (neutrophil marker) and CD123 (basophil marker) was added to the cell suspension and mixed.

Once the cuvette in complex with cuvette carrier was placed on the cuvette carrier block, 10 microliters of the mixture of white blood cells resuspended in cytometry buffer was loaded into each of two channels in the cuvette. After the mixture was loaded into channels of the cuvette, the pipette aspirated 10 μl of mineral oil from a vessel in the cartridge, and placed a drop of mineral oil on both open ends of both channels in the cuvette loaded with white blood cells.

Next, the device-level sample handling apparatus engaged the cuvette carrier/cuvette combination, and transported the cuvette carrier/cuvette combination from the module containing the cartridge to the cytometry module of the device. At the cytometry module, the device-level sample handling apparatus placed the cuvette carrier/cuvette combination on the microscopy stage of the cytometry module. After the cuvette carrier/cuvette was placed on the microscopy stage, the two channels of the cuvette containing white blood cells were imaged as described above for the RBC/platelet mixture.

Darkfield images of the white blood cells were used to count the numbers of cells in a field (as shown in FIG. 9A). Cell surface markers were used to determine the cell type of individual white blood cells in an image; for example, CD14 marks monocytes; CD123 marks basophils; CD16 marks neutrophils; and CD45-AF647 were used to mark all leukocytes (FIGS. 9B-9E). The nuclear stain Draq5 was used to mark cell nuclei, and so to differentiate nucleate cells (such as white blood cells) from mature red blood cells, which have no nucleus (FIG. 9F).

The image processing algorithms employed here utilized fluorescence images of cells to detect them using a combination of adaptive thresholding and edge detection. Based on local intensity and intensity gradients, boundaries of regions of interest (RoI) were created around each cell. Using darkfield images, beads in the sample were also identified and RoI boundaries were created around the beads. All the RoIs in each field of view were enumerated and their intensity in each image of that field of view were calculated. The information output by the image processing algorithm consisted of shape or morphometric measurements and fluorescence and darkfield intensities for each RoI. This information was analyzed using statistical methods to classify each object as a lymphocyte, monocyte, basophil, eosinophil, neutrophil or a bead. Based on enumeration of cells of different types, the corresponding bead count and the dilution ratio implemented during sample processing, an absolute concentration of cells per microliter of original whole blood was calculated. This was calculated for all white blood cells and each subtype, and reported as both absolute concentration (cells per microliter) and proportion (%).

Figure 9:
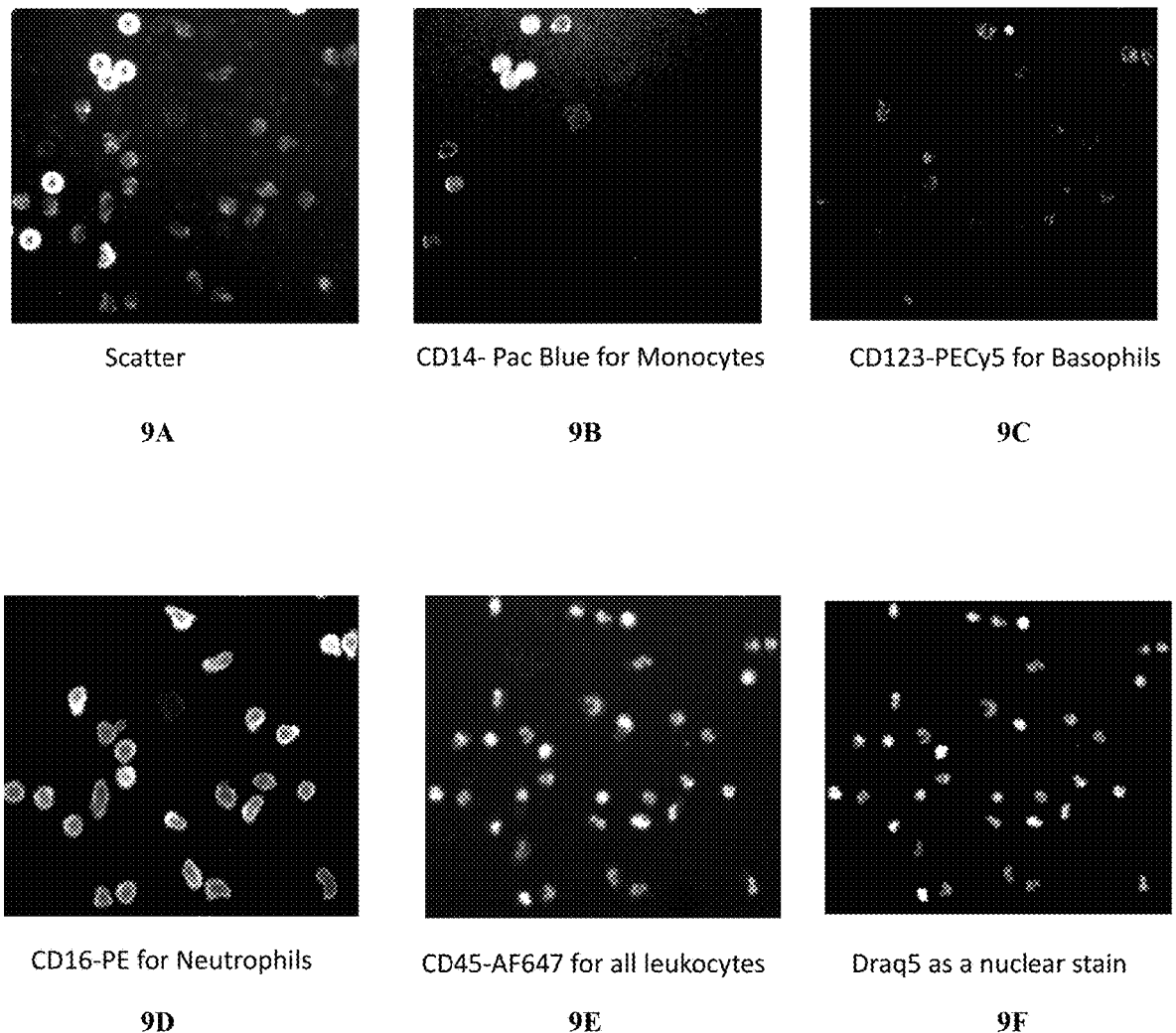
FIG. 9A is a dark-field image which shows representative images of blood cells taken from whole blood.
FIG. 9B is an image of blood cells taken from whole blood showing fluorescence from labeled anti-CD14 antibodies attached to monocytes.
FIG. 9C is an image of blood cells taken from whole blood showing fluorescence from labeled anti-CD123 antibodies attached to basophils.
FIG. 9D is an image of blood cells taken from whole blood showing fluorescence from labeled anti-CD16 antibodies attached to neutrophils.
FIG. 9E is an image of blood cells taken from whole blood showing fluorescence from labeled anti-CD45 antibodies attached to leukocytes.
FIG. 9F is an image of blood cells taken from whole blood showing leukocyte and platelet cells stained with nuclear stain Draq5 (red blood cells, lacking nuclei, are not stained by Draq5).
Figure 10:
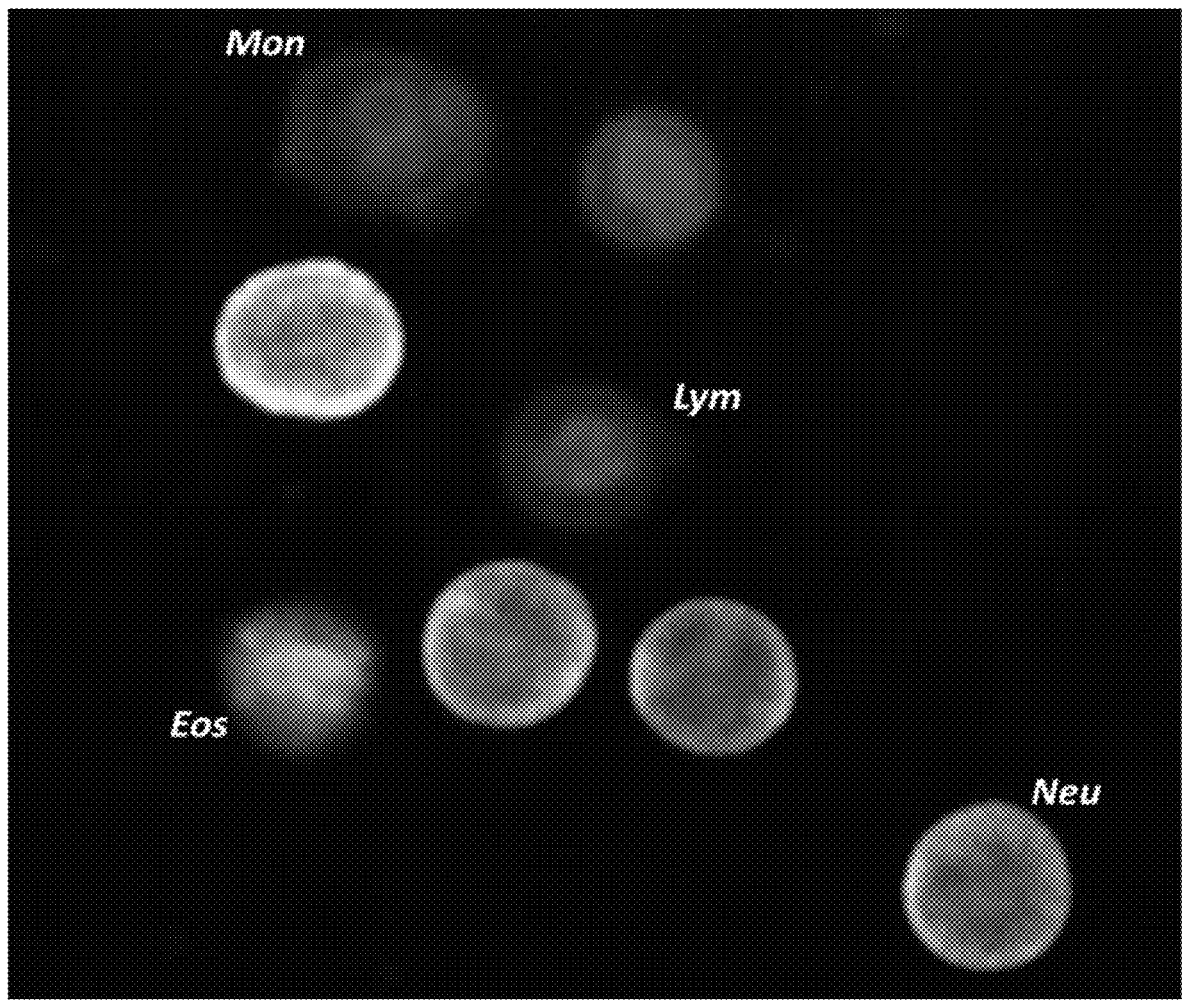
FIG. 10 is composite image which shows representative images of blood cells taken from whole blood, showing a monocyte, a lymphocyte, an eosinophil, and a neutrophil.

Examples of images and plots of results of such measurements are presented in FIGS. 9, 10, and 11.

FIG. 9 shows representative images of blood cells from a sample of whole blood; these images were taken using different imaging techniques and dyes. The image shown in FIG. 9A was taken of cells from whole blood using darkfield illumination. The image shown in FIG. 9B was taken of cells from whole blood showing fluorescence from anti-CD14 antibodies labeled with PAC Blue dye; the fluorescent cells are monocytes. The image shown in FIG. 9C was taken of cells from whole blood showing fluorescence from anti-CD123 antibodies labeled with PECy5 dye; the fluorescent cells are basophils. The image shown in FIG. 9D was taken of cells from whole blood showing fluorescence from anti-CD16 antibodies labeled with PE dye; the fluorescent cells are neutrophils. The image shown in FIG. 9E was taken of cells from whole blood showing fluorescence from anti-CD45 antibodies labeled with AF647 dye; all leukocytes fluoresce under these conditions. The image shown in FIG. 9F was taken of cells from whole blood dyed with Draq5 to stain cell nuclei. Thus, leukocytes and platelets are stained and fluoresce under these conditions, but red blood cells (lacking nuclei) are not stained and do not fluoresce.

FIG. 10 shows a representative composite image of cell-types in whole blood from images acquired according to the methods disclosed herein. Images of a monocyte (labeled and seen in the upper left quadrant of the figure, with a reddish center surrounded by a blue-purple ring), a lymphocyte (labeled and seen in the center of the figure, with a bright red center surrounded by a dimmer red ring), an eosinophil (labeled and seen in the lower left quadrant of the figure, with a green center surrounded by a red border), and a neutrophil (labeled and seen in the lower right quadrant of the figure, with a green center surrounded by a yellow and green border) are shown in the figure.

It is of interest to identify and quantify various cell types found in such blood samples. There may be multiple ways to approach such a classification process, which, in some embodiments, may be considered as being a statistical problem for multi-dimensional classification. It will be understood that a wide variety of methods are available in the field to solve these types of classification problems. A particular embodiment of such an analysis is provided below.

FIG. 11 shows plots of various cell types identified and quantified by the cytometric assays described in this example. FIG. 11A shows a plot of spots (cells) by intensity of the marker FL-17 (anti-CD14 antibody labeled with pacific blue dye) versus intensity of FL-9 (darkfield scatter signal) to identify monocytes. FIG. 11B shows a plot of spots (cells) by intensity of the marker FL-19 (anti-CD123 antibody labeled with PE-CY5 dye) versus intensity of the marker FL-15 (anti-CD16 labeled with PE dye) to identify basophils. FIG. 11C shows a plot of spots (cells) by intensity of the marker FL-15 (anti-CD16 labeled with PE dye) versus intensity of the marker FL-11 (anti-CD45 antibody labeled with AF647 dye) to identify lymphocytes. FIG. 11D shows a plot of spots (cells) by intensity of the marker FL-15 (anti-CD16 labeled with PE dye) versus intensity of FL-9 (darkfield scatter signal) to identify neutrophils and eosinophils.

Figure 11A:
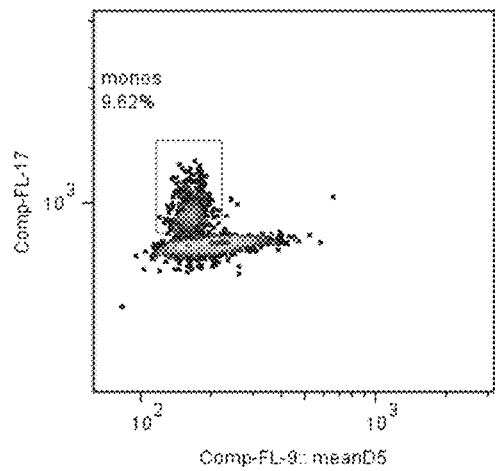
FIG. 11A shows identification of monocytes by plotting intensity of FL-17 versus FL-9 intensity. Plots of fluorescence detected on cells labeled with different markers (labeled antibodies directed at different cell-surface or other markers) are useful for identifying cells.
Figure 11B:
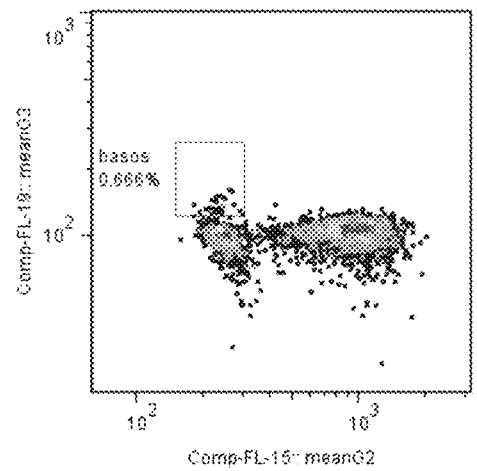
FIG. 11B shows identification of basophils by plotting intensity of FL-19 versus FL-15 intensity.
Figure 11C:
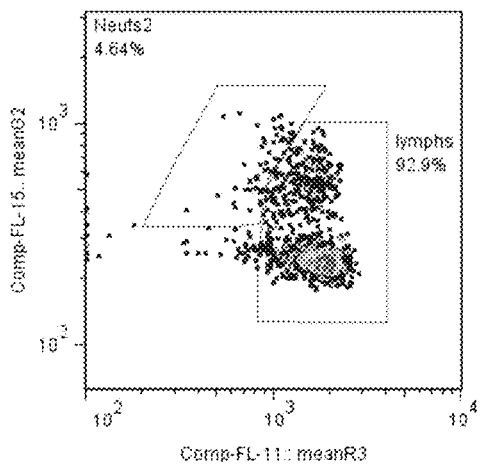
FIG. 11C shows identification of lymphocytes by plotting intensity of FL-15 versus FL-11 intensity.
Figure 11D:
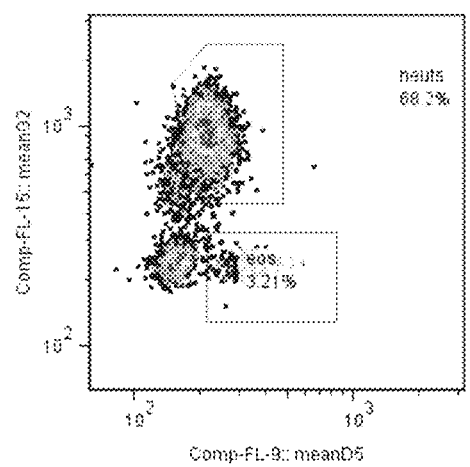
FIG. 11D shows identification of neutrophils and eosinophils by plotting intensity of FL-15 versus FL-9 intensity.

The initial identification of monocytes (9.6%, as shown in FIG. 11A) is used to guide the subsequent identification of basophils (0.68%, as shown in FIG. 11B). The identification of monocytes and basophils as shown in FIGS. 11A and 11B is used to guide the subsequent identification of neutrophils and eosinophils (68% neutrophils, 3.2% eosinophils, of the WBCs shown in FIG. 11D). Finally, lymphocytes are identified as shown in FIG. 11C (93% of the WBCs plotted in FIG. 11C, corresponding to 18% of the cells in the original sample).

The present methods correlate well with other methods. Counts of white blood cells, red blood cells, and platelets were made with samples of EDTA-anti coagulated whole blood. The white blood cells were further counted to determine the numbers of neutrophils, monocytes, and lymphocytes in the sample. In the measurements shown in FIG. 12, EDTA-anti coagulated whole blood samples were split into two, and one part of the samples were run on the system disclosed herein, using the methods disclosed herein. The other part of the samples was run on an Abbott CELL-DYN Ruby System (Abbott Diagnostics, Lake Forest, Ill., USA), a commercial multi-parameter automated hematology analyzer. A comparison of the results obtained with both methods is shown in FIG. 12.

Figure 12A:
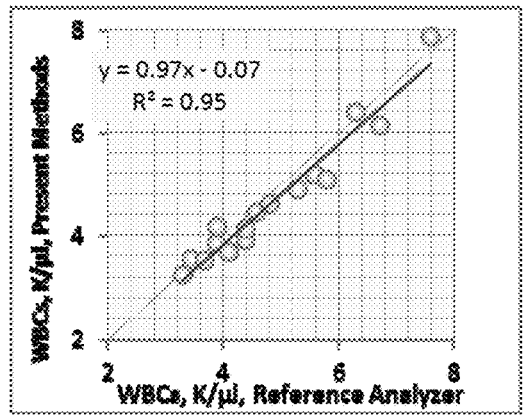
FIG. 12A plots white blood cell counts obtained by the present methods versus white blood cell counts obtained by a commercial blood analyzer. Comparisons of cell counts (measured from aliquots of the same blood sample) were obtained by the present methods, and were plotted against cell counts obtained by other methods (using a commercial blood analyzer).
Figure 12B:
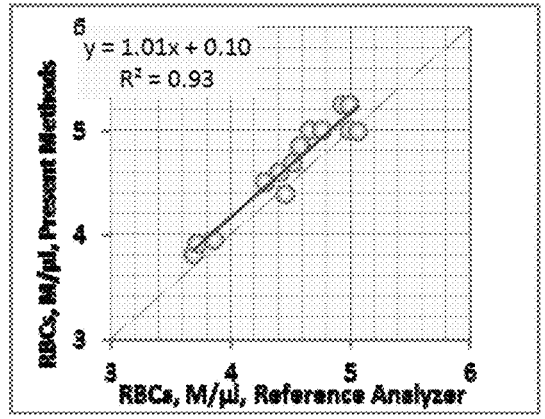
FIG. 12B plots red blood cell counts obtained by the present methods versus red blood cell counts obtained by the commercial blood analyzer.
Figure 12C:
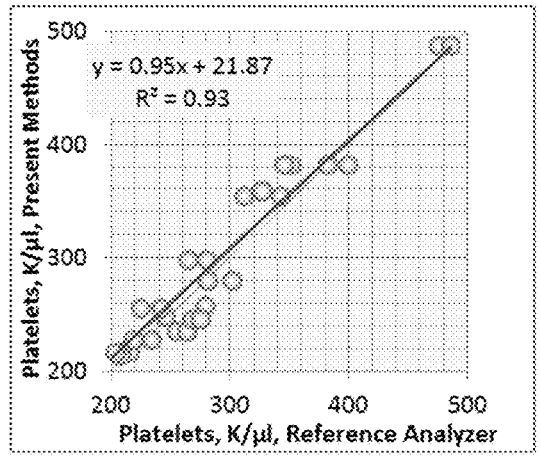
FIG. 12C plots platelet counts obtained by the present methods versus platelet counts obtained by the commercial blood analyzer.
Figure 12D:
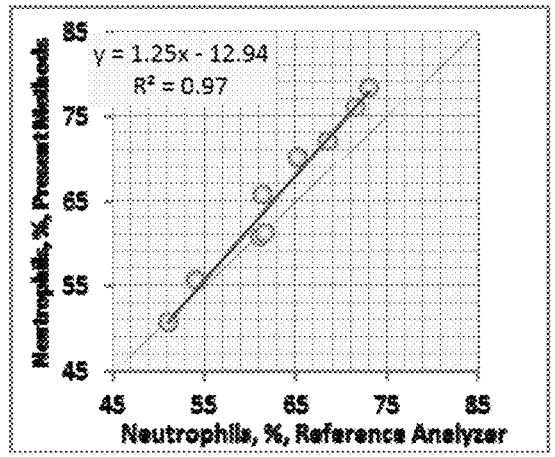
FIG. 12D plots neutrophil counts obtained by the present methods versus neutrophil counts obtained by the commercial blood analyzer.
Figure 12E:
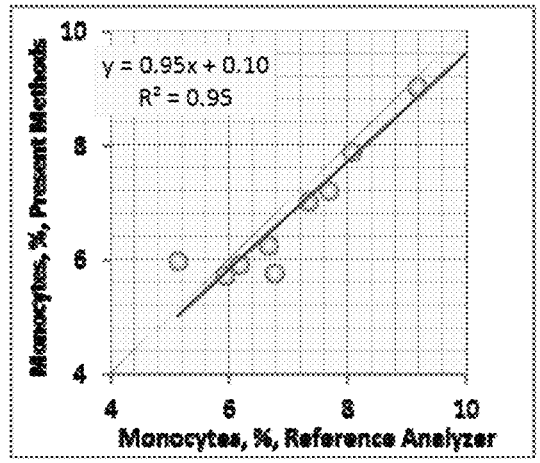
FIG. 12E plots monocyte counts obtained by the present methods versus monocyte counts obtained by the commercial blood analyzer.
Figure 12F:
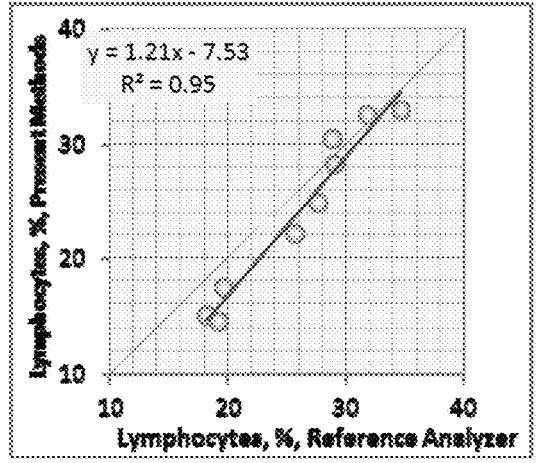
FIG. 12F plots lymphocyte counts obtained by the present methods versus lymphocyte counts obtained by the commercial blood analyzer.

As shown in FIGS. 12A-12C, the numbers of white blood cells ("WBCs", FIG. 12A), red blood cells ("RBCs", FIG. 12B) and platelets (FIG. 12C) measured by the present methods correlate well with the numbers of WBCs, RBCs, and platelets measured by other methods in corresponding aliquots of the same samples as were analyzed by the present methods. As shown in FIGS. 12D-12F, the numbers of neutrophils, monocytes, and lymphocytes measured by either method were very similar, and correlated well with each other.

In aspects of the term as used herein, the term "cytometry" refers to observations, analysis, methods, and results regarding cells of a biological sample, where the cells are substantially at rest in a fluid or on a substrate. Cells detected and analysed by cytometry may be detected and measured by any optical, electrical or acoustic detector. Cytometry may include preparing and analyzing images of cells in or from a biological sample (e.g., two-dimensional images). The cells may be labeled (e.g., with fluorescent, chemiluminescent, enzymatic, or other labels) and plated (e.g., allowed to settle on a substrate) and, typically, imaged by a camera. A microscope may be used for cell imaging in cytometry; for example, cells may be imaged by a camera and a microscope, e.g., by a camera forming an image using a microscope. An image formed by, and used for, cytometry typically includes more than one cell.

Optical Systems

Figure 6:
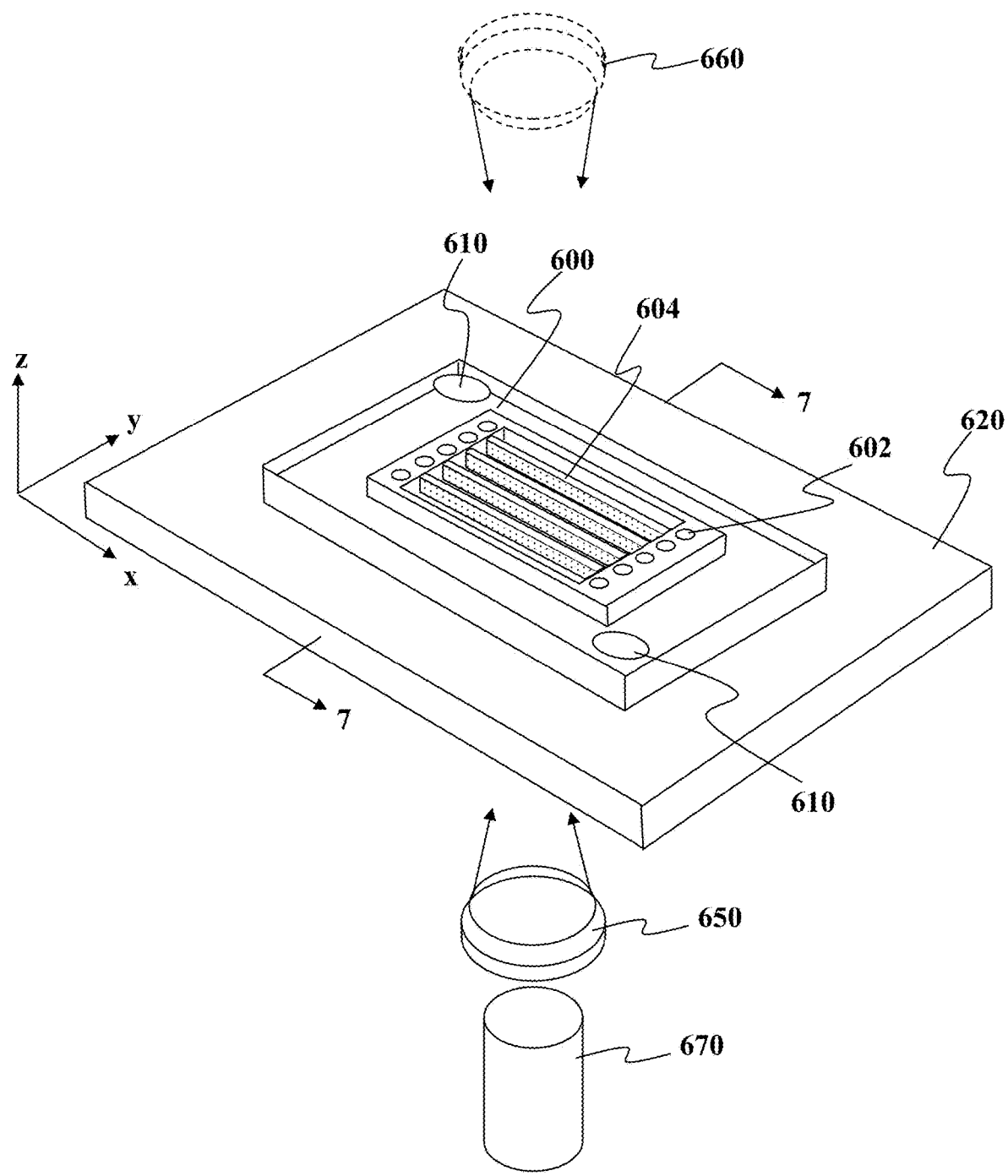
FIG. 6 shows a schematic perspective view of an embodiment of an exemplary imaging system.

Referring now to FIG. 6, one embodiment of an optical system suitable for use herein will now be described. Although this embodiment of the system is described in the context of being able to perform cytometry, it should also be understood that at least embodiments of the system also has capability beyond cytometry. By way of example and not limitation, the system can have application outside of cytometry due to the imaging and image processing capabilities associated with some embodiments. Since images are captured of the sample being analyzed and image information is typically linked or associated in the system to quantitative measurements, one can further analyze the images associated with the quantitative information to gather clinical information in the images that would otherwise be unreported.

The embodiment shown in FIG. 6 shows a perspective view of a cuvette 600 that has a plurality of openings 602 for receiving sample for analysis. Although the system is described in the context of a cuvette, it should be understood that other sample holding devices may also be used in place of or in combination with the cuvette 600.

As seen in the embodiment of FIG. 6, the openings 602 may allow for a sample handling system (not shown) or other deliver system to deposit sample into the opening 602 which may then lead to an analysis area in the cuvette where the sample can be analyzed. In one nonlimiting example, the analysis area may be a chamber. In another nonlimiting example, the analysis area may be a channel. In a still further nonlimiting example, the analysis area may be a channel wherein the sample is held in a non-flowing manner. In any of the embodiments herein, the system can hold the samples in a non-flowing manner during analysis. Optionally, some alternative embodiments may be configured to enable sample flow through the analysis area before, during, or after analysis. In some embodiments, after analysis, the sample is extracted from the cuvette 600 and then delivered to another station for further processing and/or analysis. Some embodiments may use gate(s) in the system to control sample flow.

FIG. 6 shows that some embodiments of cuvette 600 have a plurality of openings 602. Embodiments having more or fewer openings 602 in the cuvette 600 are not excluded. Some embodiments may link certain openings 602 such that select pairs or other sets of openings 602 can access the same channel. By way of nonlimiting example, there may an opening 602 at each end of an analysis area. Optionally, more than one opening 602 may be at one end of the analysis area.

Some embodiments may provide structures 604 over select areas of the cuvette 600. In one embodiment, the structures 604 are ribs that provide structural support for areas of the cuvette that are selected to have a defined thickness. The structures 604 may be use when the defined thickness areas are at a reduced thickness relative to certain areas of the cuvette and thus could benefit from mechanical support provided by structures 604.

In some embodiments, these controlled thickness areas are selected to be positioned over the analysis areas. In some embodiments, these controlled thickness areas can impart certain optical properties over or near the analysis areas. Some embodiments may configure the structures 604 to also impart optical properties on light passing through the cuvette 600. Optionally, some embodiments may configure the structures 604 to not have an impact on the optical qualities of the cuvette 600. In such an embodiment, the structures 604 may be configured to have one or more optically absorbent surfaces. For example and not limitation, certain surfaces may be black. Optionally, some embodiments may have the structures 604 formed from a material to absorb light. Optionally, the structures 604 can be positioned to provide mechanical support but do not interact with the optical properties of cuvette 600 near the analysis areas.

Some embodiments of cuvette 600 can be configured to have structures 610 that allow for a sample handling system to transport the cuvette 600. In one nonlimiting example, the structures 610 can be openings in the cuvette 600 that allow for a pipette or other elongate member to engage the cuvette 600 and transport it to the desired location. Optionally, in place of or in combination with said opening(s), the structures 610 can be a protrusion, hook, and/or other non-negative feature that can be used to engage a cuvette transport device.

It should be understood that the cuvette 600 is typically formed from an optically transparent or transmissive material. Optionally, only select portions of the cuvette 600 such as the analysis areas or areas associated with the analysis areas are optically transparent. Optionally, select layers or areas in the cuvette 600 can also be configured to be non-light transmissive.

FIG. 6 shows that in this embodiment, the cuvette 600 rests on a support structure 620 wherein at some or all of the support structure 620 is formed from an optically transparent or transmissive material. In some embodiments, the optically transparent or transmissive portions are configured to be aligned with the analysis areas of the cuvette 600 to allow for optical interrogation of the sample in the analysis area. In one nonlimiting example, the support structure 620 can be movable in the X, Y, and/or Z axis to move the cuvette 600 to a desired position for imaging. In one some embodiments, the support structure 620 comprises a platform or stage that moves only in two of the axes. Optionally, some support structures may move only in a single axis. The cuvette 600 can be configured to be operably coupled to the support structure 600 through friction, mechanical coupling, or by retaining members mounted to one or both of the components.

FIG. 6 further shows that for illumination for darkfield and/or brightfield observation, there may be an illumination source 650 such as but not limited to a ringlight below the support structure 620 to locate illumination equipment below the level of the cuvette 600. This leaves the upper areas of the cuvette 600 available for pipettes, sample handling equipment, or other equipment to have un-hindered access to openings or other features on a top surface of the cuvette 600. Optionally, some embodiment may locate an illumination source 660 (shown in phantom) above the cuvette 600 to be used in place of, in single, or in multiple combination with underside illumination source 650. An objective 670 can be positioned to observe the sample being illuminated. It should be understood that relative motion between the cuvette 600 and the optical portions 650 and 670 can be used to allow the system to visualize different analysis areas in the cuvette 600. Optionally, only one of components is in motion to interrogate different areas of the cuvette 600.

Figure 7:
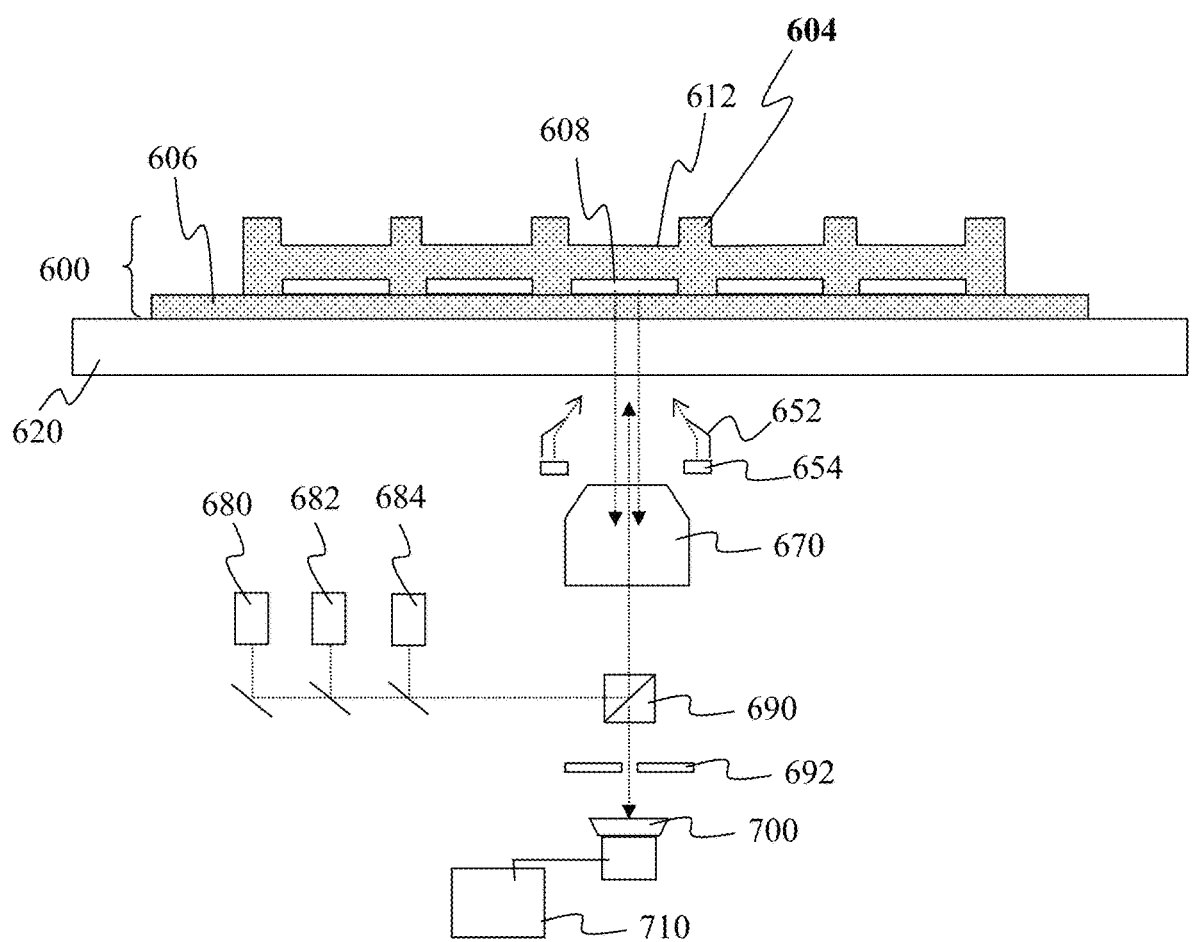
FIG. 7 shows a schematic side view (indicating cross-sections of some elements) of an embodiment of an exemplary imaging system.

Referring now to FIG. 7, one embodiment of a suitable imaging system will now be described in more detail. FIG. 7 shows a schematic cross-sectional view of various components positioned below the support structure 620. The cross-section is along the area indicated by bent arrows 7 in FIG. 6.

FIG. 6 shows that in the present embodiment, the cuvette 600 comprises a base portion 606 and analysis areas 608 defined by a cover portion 612. Optionally, the analysis areas 608 may be defined within a single piece. Optionally, the analysis areas 608 may be defined by using more than two pieces, such as but not limited a discrete cover piece for each of the analysis areas 608. In one embodiment, the layer 606 comprises optically clear plastic such as but not limited to cyclo olefin polymer thermoplastic which deliver superior optical components and applications. Some may form one or more layers or components from glass, acrylic, clear polymer, or other transparent material.

In this nonlimiting example, the sample to be interrogated can be housed in whole or in part in the area 608. By way of non-limiting example, the optics below the support structure 620 may include a ringlight 650 that comprises a toroidal reflector 652 and a light source 654. Other illumination components suitable for darkfield illumination are not excluded. Some embodiments may use a mirror. Some embodiments use a coated reflective surface. Some embodiments may use a different reflector and not a toroidal reflection. Some embodiments may use a parabolic reflector. Some embodiments may use a parabolic reflector in the shape of an elliptic paraboloid. Some embodiments may use a plurality of individual reflector pieces. Some embodiments may not use any reflector. Some embodiments obtain oblique illumination through the use of angled light sources positioned to direct light with or without further assistance from one or more external reflectors.

The embodiment of FIG. 6 shows excitation energy sources 680, 682, and 684 such as but not limited laser diodes at specific wavelengths that are mounted to direct light into the sample in analysis area 608. In one nonlimiting example to facilitate compact packaging, the energy sources 680, 682, and 684 may direct light to a dichroic 690 that then directs the excitation wavelengths into the analysis area 608. The excitation wavelength(s) cause fluorescence wavelengths to be emitted by fluorophores in marker(s), dye(s), and/or other materials in the sample. The emitted fluorescence wavelengths are funneled through the objective 670, through the dichroic 690, through an optional filter wheel 692, and into a detector 700 such as but not limited to a camera system. By way of nonlimiting example, the dichroic 690 is configured to reflect excitation wavelengths but pass fluorescence wavelengths and any wavelengths desired for optical observation.

In one embodiment, all fluorescence excitation wavelengths are illuminating the sample in analysis area 608 simultaneously. The detector 700 may be coupled to a programmable processor 710 that can take the captured signal and/or image and deconstruct which wavelengths are associated with which fluorophores that are fluorescencing. Some embodiments may have the excitation sources illuminate the sample sequentially or in subsets of the entire number of excitation sources. Of course, it should be understood that the system is not limited to fluorescence based excitation and that other detection techniques and excitation techniques may be used in place of or in single or multiple combination with fluorescence. For example, some embodiments may also collect darkfield illumination scatter information simultaneously or sequentially in combination with fluorescence detection.

Figure 8A:
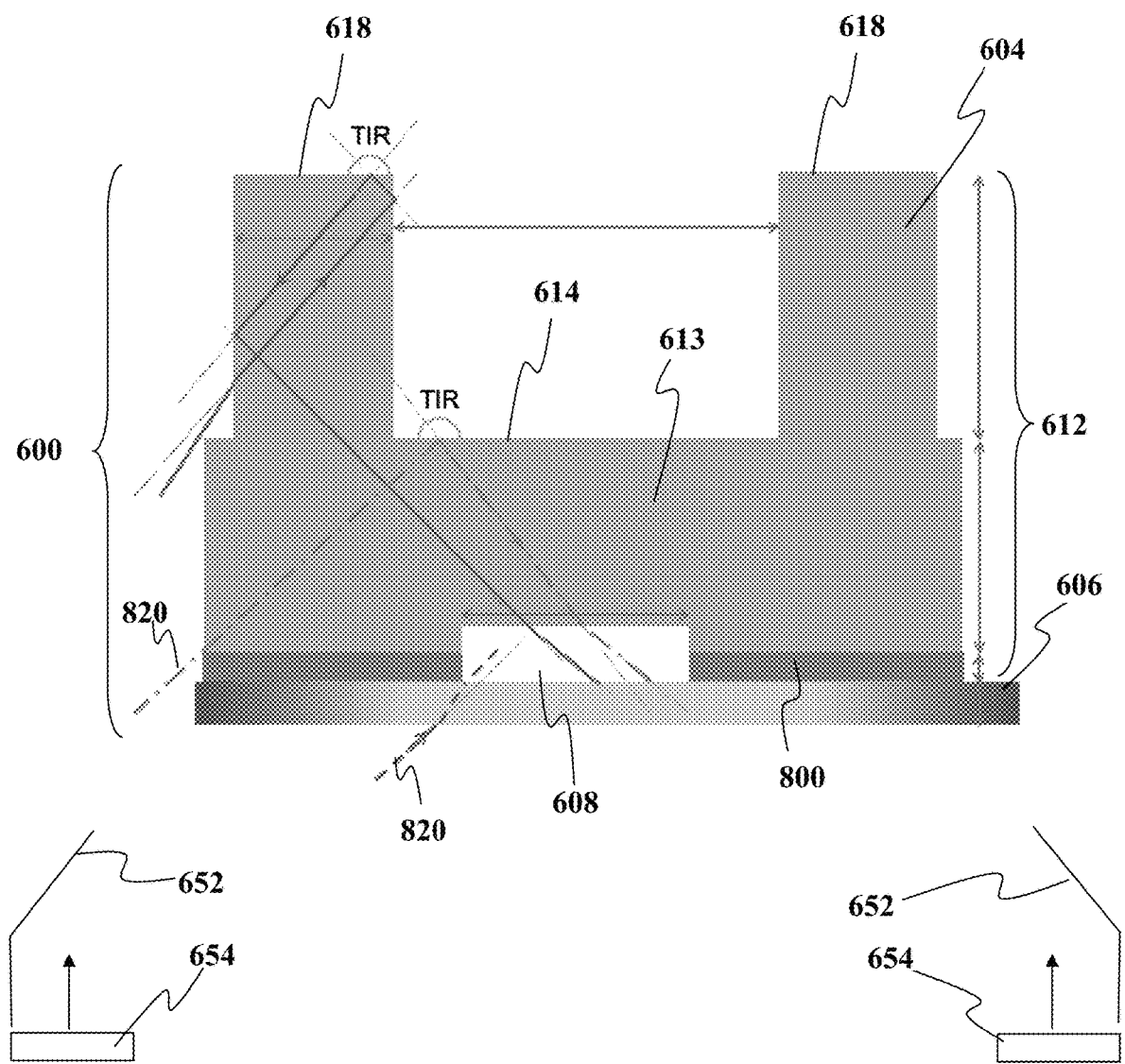
FIG. 8A shows a schematic cross-sectional side view an embodiment of an exemplary imaging system.

Referring now to FIG. 8A, a still further embodiment will now be described. FIG. 8A shows a schematic of a cross-section of a portion of the cuvette 600 and the dark field scatter illumination source such as but not limited to the ringlight 650. For ease of illustration, the support structure 620 is not shown. As seen in FIG. 8A, the ringlight 650 provides illumination for the analysis area 608. In the present embodiment, the ringlight components 652 and 654 are shown. The light source 654 may be white light or light sources such as but not limited to LEDs or laser diodes with specific wavelength output or output ranges. Optionally, the ring of light source 654 could be fiber optic cable with many splice to create a ring of light. Optionally, the light source 654 may be an LED which has specific narrow divergence angle controlled by the reflector. It may be desirable to control divergence angle from the ringlight through the selection of light source and/or design of the reflector.

By way of nonlimiting example, laser illumination as the source 654 provides for narrow light pattern with results in lower trans illumination in the present epi-style lighting configuration (where illumination components are all on one side of the sample) but because the source is a coherent source, it also lowers background signal levels. Laser illumination may not have adjacent channel illumination that typically occurs with more diffuse light sources and thus less, laser illumination can result in less trans illumination. Of course, it is desirable that the decrease in trans illumination is less than the decrease in background, where the more significant drop in background results in a more distinguishable signal. Optionally, LED as the illumination source 654 provides for a diffuse light pattern, with increased background and increased trans illumination. Of course, it is desirable that the increase in trans illumination is greater than the increase in background.

Some cuvette embodiments may include cuvettes formed from a plurality of individual layers adhered together, having the cuvette molded from one or more materials, and/or having reflective layers added to the cuvette at different surfaces to enhance multiple TIR.

Because the present embodiment may be operating in combination with fluorescence, desirable that our darkfield illumination is not white light. Some alternative embodiments may use just white light if their system is not using fluorescence detection in combination with darkfield and/or brightfield microscopy.

FIG. 8A shows that in some embodiments, the device may have layers in the cuvette 600 that are optically non-transmissive such as layer 800. This may be useful in embodiments where the light source 654 is diffuse and light is not directed to specific locations. The layer 800 can block light that are not entering the cuvette 600 at desired angles and/or locations. The layer 800 can be configured to be positioned to prevent illumination except through the area below the analysis areas 608. Some may only have specific areas that are blacked out nearest the analysis areas 608. Some embodiments may have blacked out or non-tranmissive material in more than one layer. Some may have blacked out or non-tranmissive material in different orientations, such as but not limited to one being horizontal and one being vertical or non-horizontal.

FIG. 8A shows that total-internal-reflection (TIR) may be present at an upper surface 614 and/or at surface 618 in one or more of the support structures 604. TIR is a tunable feature that can selected based on the material used for the cuvette 600 and the geometry and/or thickness of the controlled thickness area 613 of the cuvette 600. The presence of TIR which allows for oblique angle illumination coming from above the sample is desirable, particularly for darkfield microscopy. In some embodiments, it is desirable to maximize TIR from above the sample. Optionally, some embodiments may only have TIR from surfaces over the analysis areas 608. Optionally, some embodiments may only have TIR from surfaces over the controlled thickness areas 613. Optionally, some embodiments not have TIR from the support structures 604. Optionally, some embodiments not have TIR from surface 618. Optionally, some embodiments may have TIR from other surfaces in the cuvette 600, so long as it is scatter light as oblique angles being directed back to the analysis area 608.

Optionally, some embodiments may put reflective material at surfaces 614 and/or 618. Optionally, only surface 614 has reflective material on the surface. Optionally, surface 618 may be treated to be black so as to be light absorbing. Some embodiments may select the width of the controlled thickness area 612 to be wider than the analysis area 608. For some embodiments using laser illumination, the layer 800 may be removed or be light transmitting as the laser illumination is sufficiently focused so as not to require blackout between analysis areas 608.

By way of example and not limitation, the use of TIR can also enable light 820 from adjacent areas to be directed into the analysis area 608. Under traditional terminology, this is trans illumination. Line 830 shows light coming directly from the ringlight and not by way of TIR, and this is epi illumination. The combination of both types of light components from a light source located below the sample (or only one side of the sample) allows for improved performance as compared to sources that can only provide one of those lighting components. This is particularly useful for darkfield microscopy.

One nonlimiting example of the use of the embodiment shown in FIG. 8 is darkfield illumination to measure scatter properties of cells in the sample. Darkfield microscopy is an age old method that has been used mainly as a contrast enhancing technique. Since only the light scatter or reflected by the sample is imaged, the image background is fully dark. Quantitative darkfield microscopy has not been used to measure scatter properties of cells comparable to the traditional "side scatter" parameter in flow cytometers.

From the hardware perspective, illumination for darkfield microscopy is desired to be oblique, i.e. no rays of light from the illumination light source should be able to enter the objective without contacting the sample first. By way of example and not limitation, illumination should be at a wavelength that does not excite any other fluorophores already present in the sample. Optionally, this illumination allows for the use of high numerical aperture (NA) lenses for imaging. By way of example and not limitation, for traditional lens sizes associated with optical microscopes, the NA may be at least 0.3. Optionally, the NA is at least 0.4. Optionally, the NA is at least 0.5. Optionally, some embodiments may use oil immersion objective lenses to obtain a desired NA, particularly when lens size is limited below a certain level.

Traditional methods for darkfield illumination have used trans-illumination, where the sample is between the imaging lens and darkfield light source. Thus, in this embodiment, the detection and illumination components are not on the same side of the sample. The epi-illumination methods (where the imaging lens/objective and the darkfield light source are on the same side of the sample) require the use of specially manufactured objectives and typically do not allow the use of high NA objectives, thus limiting the capabilities of the whole system.

By contrast, at least some embodiments of darkfield illumination systems described herein have the following attributes. In terms of hardware, the scheme of this embodiment of FIG. 8A is "epi" in that the ringlight used for darkfield illumination is on the same side of the sample as the objective. This can be desirable from the system-perspective, although alternative embodiments with light sources on the other side may be used alone or in combination with the embodiments described herein. In one non-limiting example, the ringlight is designed such that the LEDs and/or lasers of the light source 654 are all in the same plane and have the same orientation (horizontal plane and directing light upwards). Some embodiments may have light in the sample plane but directing light in a non-parallel manner, such as but not limited to a cone-like manner. Some embodiments may have light in different planes but directing light in the same orientation. Some embodiments may have light in different planes but directing light in a non-parallel manner, such as but not limited to a cone-like manner. The light is reflected by a toroidal mirror 652 to achieve oblique illumination of the sample.

In addition to the ringlight and the toroidal reflector, the optical properties of the cuvette 600 shown in the embodiment of FIG. 8 also significantly affects darkfield illumination. In this embodiment, the cytometry cuvette 600 is designed such that light coming from the ringlight 650 is allowed to fall directly on the sample; but in addition to this, light is also "reflected" on the sample from features of the cuvette so as to emulate "trans" illumination. This reflection can be by way of TIR and/or true reflection.

Note that any trans-illumination scheme allows one to measure forward scattered light from a particle whereas an epi-scheme allows one to measure only the back-scattered light. Forward scattered light is generally two orders of magnitude greater in intensity than the back-scattered light. Trans-scheme thus allows the use of much lower illumination intensities and reduces harmful side effects on the sample.

As seen in the embodiment of FIG. 8A, the ringlight 650 and cuvette 600 provide a system that can be tuned such that the intensities of trans and epi illumination are adjusted for improved performance over traditional epi illumination. This tuning can be achieved by virtue of cuvette geometry to control angles and extent of total internal reflection and material properties.

Figure 8B:
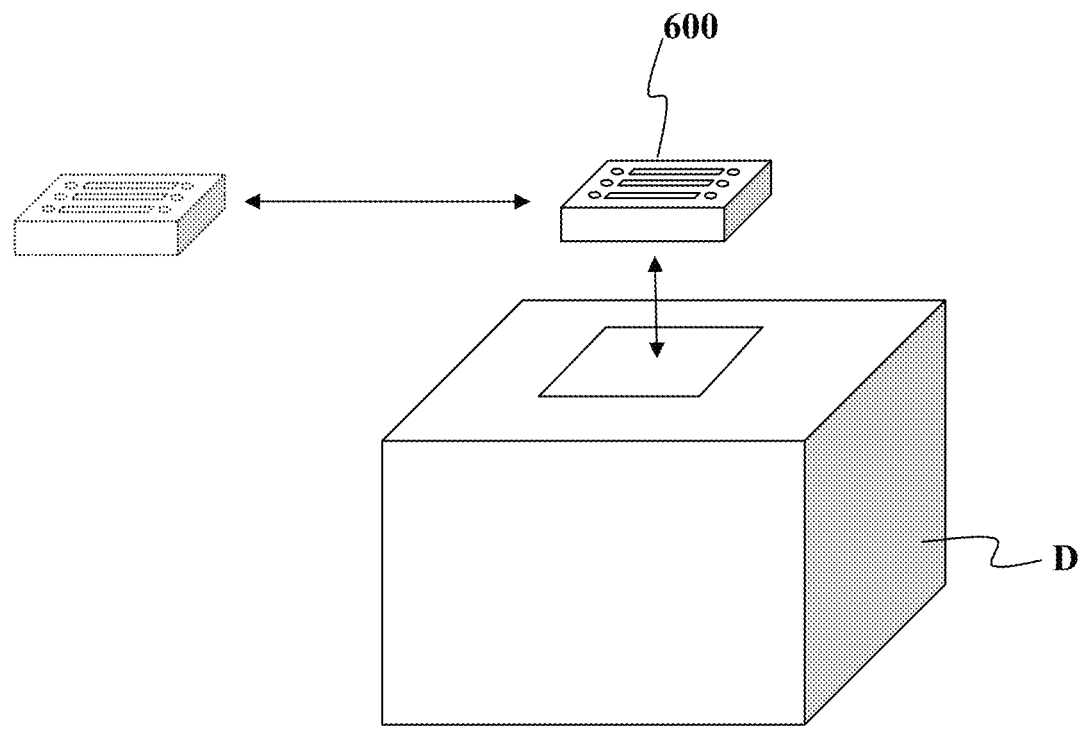
FIG. 8B shows a schematic perspective view an embodiment of an exemplary imaging system.
Figure 8C:
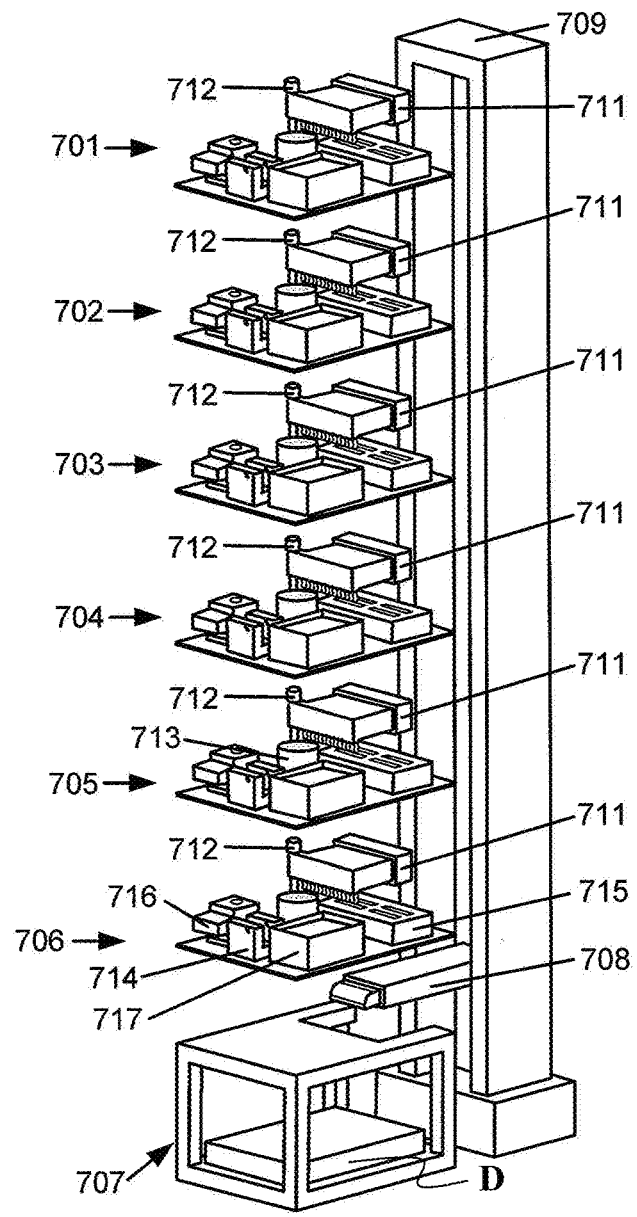
FIG. 8C shows a schematic perspective view an embodiment of an exemplary system including an imaging system.

FIGS. 8B and 8C show that the sample holder such as cuvette 600 is transported from one location such as where sample preparation may occur and then to the detector D as seen in FIGS. 8B and 8C. The cuvette 600 does not release fluids into or onto the detector D, but instead is self-contained unit that keeps all of the sample therein. There may be one or more, two or more, or three or more locations on the detector D on which there is transparent surface on which the cuvette 600 or other sample holder can engage to provide a transparent interface for sample signal detection to occur. The elements of FIG. 8C can be found in reference to U.S. patent application Ser. No. 13/769,779 fully incorporated herein by reference.

Darkfield

At least some embodiments herein include a dark field illumination source and cuvette. The relevant features of the cuvette 600 relate to designing the cuvette dimensions and optical materials and the geometry of the cuvette. The cuvette increases the extent of darkfield illumination through total internal reflection (TIR) and/or pure reflection. In one embodiment, the system may simultaneously use trans darkfield and epi darkfield.

In some embodiments herein, the cuvette combined with the light source enables trans and epi illumination using only physical system in epi configuration (light source on one side of sample). The basic cuvette is designed to contain the biological sample and present it for visualization. In one embodiment, the coverslip 612 may have a specific design. Materials have different index of refraction. Some embodiments may make cover slip 612 of glass.

One can design the material of the top coverslip 612 to facilitate illumination and image collection. To get light to the cells, the ringlight 650 may be circular, have light sources 654 position in a discrete or continuous pattern, and use a curved reflector 652 to direct light to the sample.

In darkfield microscopy, the sample is illuminated by oblique rays. The light going into the microscopy is the light scattered by the sample. Measuring scatter properties of the cells. If nothing is there, the image is black.

In the present non-limiting example, the reflector 652 and LED 654 of the ringlight 650 are designed to reflect so that a minimum fraction goes directly back into the objective as non-specific background. The system is designed to give TIR surface and reflection from other surfaces back into the target area 608. The cells in the sample in 608 is getting light directly from the ringlight from underneath the cell (this is epi). There is also light coming from the top surfaces (reflected) and this is trans.

With the ringlight 650 in the same position, one now has light coming from two directions from a single ringlight source. This is all oblique. One can control the relative strengths of the two light components by design of the cuvette and material used for the cuvette.

This darkfield illumination is different from conventional darkfield. By way of nonlimiting example, this embodiment may use a reflective layer on the backside of certain surfaces of the coverslip 612 to reflect all of the light. Some embodiments may use a full or selectively reflective background.

In the present embodiment, the light is desirable at an oblique angle which keeps illumination darkfield. Some may angle the light sources 654 at an angle and thus not use the reflector 652. The reflector 652 may improve manufacturability of the light source 654 since all lights are in the same plane, directed in the same direction. Optionally, the angled light sources 654 may also be used in place of or in combination with a reflector.

It should be understood that here even though trans component may be in one example 10 times weaker than epi illumination component, the scatter from the cells in the sample due to trans may be 200 times stronger from the same amount of epi versus scatter from the same amount of trans. And thus, the small amount of trans can significantly enhance the scatter from cells. The light collected from epi illumination also does not include defraction. Defraction is a substantial component of scatter and the use of trans illumination provides for some amount diffraction. Thus, there is reflective, refractive, and defractive components when using trans and epi illumination. With epi alone, there may be only reflective. Traditional methods uses all trans darkfield illumination which takes significant amount of space to configure, due to components being on both sides of the sample. The present embodiment may obtain the space savings of an epi configuration but still have epi and trans illumination components on the sample.

Designing the sample holder and the light source together can enable an epi configuration to increase the amount of trans illumination, particularly uniform trans illumination. Some embodiment may use mirrored surfaces but TIR can be tuned to create the desired trans lighting that is uniform and at oblique angles into the analysis area for darkfield illumination of the sample. In one nonlimiting example, a thicker top 612 allows the TIR to come back into the target area 608. Traditional hardware may have some TIR but the light may not come back into the area 608. Additionally, not just that TIR illumination comes back into the channel but that it comes back uniformly. This embodiment of FIG. 8 has certain surfaces at certain angles, has certain black surface(s), and certain reflective surface(s) so that the light comes back uniformly. Optionally, one could put a fully reflective surface on a top (such as but not limited to a flat top but optionally over select areas of top 612 such as area 613).

By way of nonlimiting example, embodiments here take an imaging based platform and instead of using a high complication, high cost system which may for example have 16 laser, the present embodiment leverages a more integrated detection system to be able to pick-up the differentials of cells and types.

In one nonlimiting example, it is the combination of all these different types of information to achieve the clinical goals. This may include quantitative and/or qualitative linked to quantitative, or images linked to quantitative measurements. Not only different channels of fluorescence where each channel may have one or more specific molecular markers targeted and that is quantitative information, but with microscopy, some embodiments herein have the ability to look at the background that staining forms inside the cell (whether it is in the cytoplasm, is it concentrated on the surface, in the nucleus) that can link image and/or qualitative information that generated the quantitative measurements. In this manner, the linkage of the original images that created the quantitative results are available for further analysis if it turns out that the quantitative measurements trigger alarms or meet thresholds the suggest further analysis is desired. Embodiments herein can interrogate background staining creates in the cell. One can image if the staining is in the cell, the cytoplasm, etc. . . . . .

Some embodiments herein may be combining the quantitative scatter properties of the cell, the shape of the cell, and/or the size of the cell. Some embodiments here measure the physical properties, optical properties, and bio/biochemical properties all in the same device at the same time. All can be combined in a programmable processor or other processing system link the various types of information to achieve the clinical goal of the assays.

Many traditional devices do one or the other. They do not do both and there is also no linkage between different types of information. Some embodiments herein, where image information is retrievable that generated the quantitative measurements, can be extended to tissue morphology measurement. Optionally, the system can be applied to pap smear, which is more similar to traditional cytology. It can be extended to anything done using traditional microscopy. In urine, at least some of the present embodiments can look at and analyze crystals and not just cells. One can look at crystals of inorganic salts and chemicals from urine samples that had created certain quantitative readings on one portion of a graph, such as but not limited what may be seen in FIG. 1A where different regions of data are circled. Image information for certain data regions can be retrieved to further analyze the underlying cell images that created the measurements plotted on the graph or chart.

Some embodiments herein combine the imaging features with the pathology features. For example, tissue prep may occur inside a blade or module, and such prepped material can be imaged in this platform. Then the images or analysis is sent to servers to do image analysis to do diagnosis or digital pathology to enable a pathologist to do analysis.

Esoteric Cytometry and Specialty Cytometry Marker

Many traditional advanced or esoteric cytometric assays require a traditional system to measure a large number of markers on cells, typically simultaneously. The general approach in the field have been tied to high capability instruments such as six or other multiple numbers of lasers and 18 different PMT tubes to measure all of these parameters simultaneously. Part of it has been dictated by traditional methodology of identifying all markers on a cell at the same time, which has driven it. However, in many clinical settings, this simultaneous measurement is not the requirement. In many clinical requirements, one is interested in seeing how many cells are positive for one marker, how many are positive for a combination of two or three markers. Some embodiments herein provide for multiple combinations of staining schemes where one may have a set of, for example, 10 markers, where one can combine them in sets of 3-4 or 5-6 markers where one can combine them such that even if combining two markers in the same color, some embodiments of the present system can de-convolute which signal came from which marker. This allows some embodiments of the present system to reduce the hardware requirements in terms of the number of light sources, the number of channels used for sample analysis. Thus, using subsets or markers in non-simultaneous manner in a pre-determined pairing can be useful to enable esoteric cytometry. Perhaps certain markers are "gating" markers and they can be tested first and if the results are negative, then other follow-on markers may not be need. Some embodiments herein using this non-simultaneous system also reduces the sample volume requirement.

It should be understood that by using imaging, the ability to get an actual count, it may be more accurate than traditional cytometry. Traditional flow cytometry gating does not allow for actual count. Imaging can actually be more accurate. The gating in flow cytometry is subjective and thus this can vary from system to system.

Some embodiments herein may also gate, but the gating is based algorithmically based on various factors including but not limited to patient health. Classification means is trained on a population of patients knowing if they are healthy or diseased. Some embodiments here can flag a patient that is abnormal and flagging it for review. Self learning gating can determine if different gating is desired based on information conveyed regarding the patient health.

Thus, the gating for some embodiments herein for the sample is done algorithmically, possibly with a programmable processor, and the gating changes based on patient health.

Imaging: in many cases, one may want to minimize hardware capability and to re-use the sample volume. Thus, the more capability one can extract from the imaging, the better in terms maximizing information from even less sample. Thus, the more information one can get to differentiate different cell types from minimum number of pictures, the more one may minimize the sample volume required.

Optionally, in one non-limiting example, the cuvette for use in the microscopy stage can be configured as follows. The middle channel layer comprises a core of thin plastic membrane 800 with pressure-sensitive-adhesive (psa) on both sides. One side adheres to the window-layer 606 and the other side to the molded-top-layer. The core is an extruded film that is black in color, primarily due to optical reasons of preventing light scatter and optical cross-talk between the different liquid channels. This core membrane has to have good (small) thickness control and is typically formed from an extruded film of black PET or black HDPE (polyethylene). The psa sub-layers on both sides have to be as thin as possible for preserving the tight thickness control of the overall liquid channel, yet thick enough to provide a good fluidic seal around the liquid channel. The psa adhesives found best for our design were acrylic in nature and had high adhesion strength for low-surface-energy plastics. The liquid channels, ports and other alignment features on the middle layer were fabricated using laser-cutting or die-cutting processes.

This embodiment also shows that magnetic feature(s) such as but not limited to pucks or discs may be incorporated into the cuvette, such as but not limited to being the molded top layer. This can be used to simplify hardware use to transport the cuvette. Here, the handling system can engage the magnetic features in the cuvette to transport it without having to add an additional sample handling device.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, different materials may be used to create different reflective surfaces in the cuvette or other surfaces along a light pathway in the optical system. Optionally, the reflective surface is selected so that the reflection is only diffusive. Optionally, the reflective surface is selected so that the reflection is only specular. Some embodiment may use a flat top illumination scheme as set forth in Coumans, F. A. W., van der Pol, E., & Terstappen, L. W. M. M. (2012), Flat-top illumination profile in an epifluorescence microscope by dual microlens arrays. Cytometry, 81A: 324-331. doi: 10.1002/cyto.a.22029, fully incorporated herein by reference for all purposes.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, etc. . . .

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are also incorporated herein by reference for all purposes: U.S. Pat. Nos. 7,888,125, 8,007,999, 8,088,593 and U.S. Publication No., US20120309636, PCT Application No. PCT US2012/057155, U.S. patent application Ser. No. 13/244,952, and PCT Application No. PCT/US2011/53188, filed Sep. 25, 2011, U.S. patent application Ser. No. 13/244,946, filed Sep. 26, 2011, PCT Application No. PCT/US11/53189, filed Sep. 25, 2011, Patent Cooperation Treaty Application No. PCT/US2011/53188; Patent Cooperation Treaty Application No. PCT/US2012/57155; U.S. patent application Ser. No. 13/244,947; U.S. patent application Ser. No. 13/244,949; U.S. patent application Ser. No. 13/244,950; U.S. patent application Ser. No. 13/244,951; U.S. patent application Ser. No. 13/244,952; U.S. patent application Ser. No. 13/244,953; U.S. patent application Ser. No. 13/244,954; U.S. patent application Ser. No. 13/244,956; and U.S. patent application Ser. No. 13/769,820, entitled "Systems and Methods for Multi-Purpose Analysis," filed Feb. 18, 2013, all of which applications are hereby incorporated by reference in their entireties. The following applications are fully incorporated herein by reference for all purposes: U.S. Pat. Nos. 8,088,593; 8,380,541; U.S. patent application Ser. No. 13/769,798, filed Feb. 18, 2013; U.S. patent application Ser. No. 13/769,779, filed Feb. 18, 2013; U.S. Pat. App. Ser. No. 61/766,113 filed Feb. 18, 2013, U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. Application Ser. No. 61/673,245, filed Sep. 26, 2011, U.S. Patent Application Ser. No. 61/786,351 filed Mar. 15, 2013, U.S. Patent Application Ser. No. 61/697,797 filed Sep. 6, 2012, and U.S. Patent Application Ser. No. 61/733,886 filed Dec. 5, 2012, the disclosures of which patents and patent applications are all hereby incorporated by reference in their entireties for all purposes.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise. Thus, in contexts where the terms "and" or "or" are used, usage of such conjunctions do not exclude an "and/or" meaning unless the context expressly dictates otherwise.

What is claimed is:

1. A method for the measurement of at least two components of interest in cells of a cellular population in a sample, comprising:
  a) obtaining, with a different modality from that used for cytometry, a quantitative measurement of a first component of interest present in cells of the cellular population in the sample;
  b) based on the measurement of part a), determining, with the aid of a computer, an approximate number of cells in the cellular population present in the sample;
  c) based on the results of part b), i) adding an amount of a first cell marker that binds to a second component of interest and is configured to be readily detectable, and ii) adding an amount of a second cell marker that binds to a third component of interest, wherein the second component of interest is different than the third component of interest;
  d) assaying cells in the sample for the first cell marker bound to the second component of interest, wherein said assaying comprises use of a detector;
  e) assaying cells in the sample for the second cell marker bound to the third component of interest, wherein said assaying comprises use of the detector;
  f) based on the amount of first cell marker bound to the second component of interest, determining the amount of the second component of interest in cells of the cellular population of the sample; and
  g) based on the amount of the second cell marker bound to the third component of interest, determining the amount of the third component of interest in cells of the cellular population of the sample;
  wherein the first component of interest is different from the second component of interest and the third component of interest;
  wherein the second component of interest is selected from one of the following: leukocyte, neutrophil, natural killer cell, platelet, white blood cell, T cell, B cell, monocyte, lymphocyte, eosinophil, or basophil;
  wherein the third component of interest is selected from one of the following: leukocyte, neutrophil, natural killer cell, platelet, white blood cell, T cell, B cell, monocyte, lymphocyte, eosinophil, or basophil.

2. The method of claim 1, wherein the first cell marker comprises a labeled antibody or labeled antibody fragment.

3. The method of claim 2, wherein said labeled antibody or labeled antibody fragment comprises a fluorescently labeled antibody or a fluorescently labeled antibody fragment.

4. The method of claim 1, wherein said sample is held in a sample holder configured to receive light from an illumination source to provide both trans-illumination and epi-illumination to the sample, wherein the illumination source is positioned to illuminate substantially only one side of the sample holder.

5. The method of claim 4, wherein total internal reflection is used to provide said trans-illumination to the sample.

6. The method of claim 5, wherein said total internal reflection used to provide trans-illumination to the sample comprises total internal reflection within the sample holder.

7. The method of claim 1 wherein the sample is held in a sample holder, wherein the sample remains separate from a detector in a fluid circuit fully confined in the sample holder, where the sample holder is movable relative to the detector.

8. The method of claim 1, wherein measurement of a component of interest comprises use of fluorescence microscopy and of dark field microscopy.

9. The method of claim 1, wherein said different modality comprises use of a spectrophotometer.

10. A method for the measurement of at least two components of interest in cells of a cellular population in a sample, comprising:
   a) obtaining, with a different modality from that used for cytometry, a quantitative measurement of a component of interest present in cells of the cellular population in the sample;
   b) based on the measurement of part a), determining, with the aid of a computer, an approximate number of cells in the cellular population present in the sample;
   c) based on the results of part b), i) adding an amount of a first cell marker that binds to a second component of interest, and ii) adding an amount of a second cell marker that binds to a third component of interest, wherein the second component of interest is different than the third component of interest;
   d) assaying cells in the sample for the first cell marker bound to the second component of interest, wherein said assaying comprises use of a detector;
   e) assaying cells in the sample for the second cell marker bound to the third component of interest, wherein said assaying comprises use of the detector;
   f) based on the amount of first cell marker bound to the second component of interest, determining the amount of the second component of interest in cells of the cellular population of the sample; and
   g) based on the amount of the second cell marker bound to the third component of interest, determining the amount of the third component of interest in cells of the cellular population of the sample;
   wherein the first cell marker comprises a labeled antibody and the second cell mark comprises another labeled antibody;
   wherein the component of interest in step a) is different from the second component of interest and the third component of interest;
   wherein the second component of interest is selected from one of the following: leukocyte, neutrophil, natural killer cell, platelet, white blood cell, T cell, B cell, monocyte, lymphocyte, eosinophil, or basophil;
   wherein the third component of interest is selected from one of the following: leukocyte, neutrophil, natural killer cell, platelet, white blood cell, T cell, B cell, monocyte, lymphocyte, eosinophil, or basophil.

11. A method for the measurement of at least two components of interest in cells of a cellular population in a sample, comprising:
   a) obtaining, with a different modality from that used for cytometry, a quantitative measurement of a component of interest present in cells of the cellular population in the sample;
   b) based on the measurement of part a), determining, with the aid of a computer, an approximate number of cells in the cellular population present in the sample;
   c) based on the results of part b), i) adding an amount of a first cell marker that binds to a second component of interest, and ii) adding an amount of a second cell marker that binds to a third component of interest, wherein the second component of interest is different than the third component of interest;
   d) assaying cells in the sample for the first cell marker bound to the second component of interest, wherein said assaying comprises use of a detector;
   e) assaying cells in the sample for the second cell marker bound to the third component of interest, wherein said assaying comprises use of the detector;
   f) based on the amount of first cell marker bound to the second component of interest, determining the amount of the second component of interest in cells of the cellular population of the sample; and
   g) based on the amount of the second cell marker bound to the third component of interest, determining the amount of the third component of interest in cells of the cellular population of the sample;
   wherein the first cell marker comprises a labeled antibody fragment and the second cell mark comprises another labeled antibody fragment;
   wherein the component of interest in step a) is different from the second component of interest and the third component of interest;
   wherein the second component of interest is selected from one of the following: leukocyte, neutrophil, natural killer cell, platelet, white blood cell, T cell, B cell, monocyte, lymphocyte, eosinophil, or basophil;
   wherein the third component of interest is selected from one of the following: leukocyte, neutrophil, natural killer cell, platelet, white blood cell, T cell, B cell, monocyte, lymphocyte, eosinophil, or basophil.

12. The method of claim 11 wherein the sample is held in a sample holder, wherein the sample remains separate from a detector in a fluid circuit fully confined in the sample holder, where the sample holder is movable relative to the detector.

13. The method of claim 11, wherein measurement of a component of interest comprises use of fluorescence microscopy and of dark field microscopy.

14. The method of claim 11, wherein said different modality comprises use of a spectrophotometer.

15. The method of claim 10, wherein measurement of a component of interest comprises use of fluorescence microscopy and of dark field microscopy.

16. The method of claim 10, wherein said different modality comprises use of a spectrophotometer.

* * * * *